(12) United States Patent
Kuramoto

(10) Patent No.: US 9,509,964 B2
(45) Date of Patent: Nov. 29, 2016

(54) ENDOSCOPE SYSTEM AND LIGHT SOURCE DEVICE

(71) Applicant: FUJIFILM Corporation, Tokyo (JP)

(72) Inventor: Masayuki Kuramoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 280 days.

(21) Appl. No.: 14/338,999

(22) Filed: Jul. 23, 2014

(65) Prior Publication Data

US 2015/0092033 A1    Apr. 2, 2015

(30) Foreign Application Priority Data

Sep. 27, 2013 (JP) ................................. 2013-202554

(51) Int. Cl.
| | |
|---|---|
| *H04N 9/04* | (2006.01) |
| *H04N 5/225* | (2006.01) |
| *H04N 5/372* | (2011.01) |
| *A61B 1/05* | (2006.01) |
| *A61B 1/00* | (2006.01) |
| *A61B 1/06* | (2006.01) |

(52) U.S. Cl.
CPC ............ *H04N 9/045* (2013.01); *A61B 1/0002* (2013.01); *A61B 1/00009* (2013.01); *A61B 1/00057* (2013.01); *A61B 1/051* (2013.01); *A61B 1/0684* (2013.01); *H04N 5/2256* (2013.01); *H04N 5/372* (2013.01); *H04N 2005/2255* (2013.01)

(58) Field of Classification Search
CPC .............. A61B 1/0638; A61B 1/0684; A61B 1/00009; A61B 90/361; A61B 2576/00; A61B 17/3478; A61B 5/0075; A61B 1/0661; H04N 13/0203; G06T 2207/10068
See application file for complete search history.

(56) References Cited

U.S. PATENT DOCUMENTS

| | | | |
|---|---|---|---|
| 8,531,512 B2 | 9/2013 | Gono et al. | |
| 2007/0102623 A1* | 5/2007 | Fengler | A61B 1/00009 250/208.1 |
| 2008/0174701 A1* | 7/2008 | Iketani | A61B 1/05 348/687 |
| 2009/0141125 A1 | 6/2009 | Yamazaki | |
| 2012/0271103 A1* | 10/2012 | Gono | A61B 1/00163 600/109 |

* cited by examiner

*Primary Examiner* — Hung Dang
*Assistant Examiner* — Sunghyoun Park
(74) *Attorney, Agent, or Firm* — Birch, Stewart, Kolasch & Birch, LLP

(57) ABSTRACT

Violet narrowband light Vn and green narrowband light Gn produced by a light source device are supplied to a complementary color type endoscope, and simultaneously applied to an observation object. From a complementary color type imaging device, first mixed pixels and second mixed pixels, which sense both of the violet narrowband light Vn and the green narrowband light Gn, are read out. The light amount ratio Z of the violet narrowband light Vn to the green narrowband light Gn is set within a predetermined range based on an optimal light amount ratio $Z_0$ at which the proportion P1 of a violet narrowband light Vn component within a first mixed pixel signal becomes equal to the proportion P2 of a green narrowband light Gn component within a second mixed pixel signal. This improves color separability of an endoscope system.

17 Claims, 14 Drawing Sheets

ENDOSCOPE SYSTEM AND LIGHT SOURCE DEVICE

CROSS-REFERENCE TO RELATED APPLICATIONS

The present application claims priority under 35 U.S.C §119 to Japanese Patent Application No. 2013-202554 filed on Sep. 27, 2013. The above application is hereby expressly incorporated by reference, in its entirety, into the present application.

BACKGROUND OF THE INVENTION

1. Field of the Invention

The present invention relates to an endoscope system for performing narrowband light observation using a complementary color type imaging device, and a light source device used in the endoscope system.

2. Description Related to the Prior Art

In a recent medical field, diagnosis and treatment using an endoscope system, having a light source device, an electronic endoscope, and a processor device, are widely performed. The light source device produces illumination light and applies the illumination light to the inside of a human body cavity. The electronic endoscope images the inside of the body cavity irradiated with the illumination light by an imaging device, and produces an imaging signal. The processor device applies image processing to the imaging signal produced by the electronic endoscope to produce an observation image to be displayed on a monitor.

As an observation method used in the endoscope system, there is known narrowband light observation using special light (narrowband light) having a narrow wavelength band as the illumination light, in addition to normal light observation using normal light (white light) having a wide wavelength band as the illumination light. The narrowband light observation, for example, can improve visibility of a blood vessel pattern in a superficial layer of a mucosa membrane, though the blood vessel pattern is easily buried in optical information obtained under irradiation with the white light. Therefore, the narrowband light observation allows focusing attention on superficial blood vessels of the blood vessel pattern, and diagnosing the stage of a disease, the depth of a lesion, and the like from the state of the superficial blood vessels.

The narrowband light observation uses two types of narrowband light absorbable by hemoglobin in blood, that is, blue narrowband light having a center wavelength in the vicinity of 415 nm and green narrowband light having a center wavelength in the vicinity of 540 nm. As an imaging method in the narrowband light observation, there are known a frame sequential method in which the blue narrowband light and the green narrowband light are alternately applied and a monochrome imaging device captures an image whenever each type of light is applied, and a simultaneous method in which the blue narrowband light and the green narrowband light are simultaneously applied and a simultaneous imaging device having a color filter captures an image (see U.S. Pat. No. 8,531,512 and US Patent Application Publication No. 2009/0141125). The simultaneous method is inferior in resolution to the frame sequential method, but has the advantages of preventing a blur in the image and structural simplicity of the endoscope system.

The simultaneous imaging device includes a primary color type imaging device having a primary color filter and a complementary color type imaging device having a complementary color filter. The complementary color type imaging device is highly sensitive as compared with the primary color type imaging device, and hence used in an endoscope system that places importance on sensitivity.

The U.S. Pat. No. 8,531,512 and the US Patent Application Publication No. 2009/0141125 disclose a complementary color type imaging device having four types of pixels of magenta (Mg), green (G), cyan (Cy), and yellow (Ye) in which the Mg pixels and the G pixels are alternately arranged in odd-number rows, and the Cy pixels and the Ye pixels are alternately arranged in even-number rows, such that the Mg pixel, the Cy pixel, the Mg pixel, the Ye pixel, . . . are arranged in this order in odd-number columns, and the G pixel, the Ye pixel, the G pixel, the Cy pixel . . . are arranged in this order in even-number columns. This color filter pattern is referred to as a complementary-color checkered-pattern color-difference line sequential method.

This complementary color type imaging device is driven by a field readout method in which pixel signals of two rows adjoining in a column direction are read out in a mixed (added) state in each of an odd-number field and an even-number field. Thus, the complementary color type imaging device outputs a mixed pixel signal (hereinafter called a first mixed pixel signal) of the Mg pixel and the Cy pixel, a mixed pixel signal (hereinafter called a second mixed pixel signal) of the G pixel and the Ye pixel, a mixed pixel signal (hereinafter called a third mixed pixel signal) of the Mg pixel and the Ye pixel, and a mixed pixel signal (hereinafter called a fourth mixed pixel signal) of the G pixel and the Cy pixel. The complementary-color checkered-pattern color-difference line sequential method has the advantage that the first to fourth mixed pixel signals are easily converted into a primary color signal (RGB signal) by a simple operation.

However, in the case of the narrowband light observation, the above complementary color type imaging device has a problem of mixture of the blue narrowband light and the green narrowband light. As for the blue narrowband light, for example, out of the above first to fourth mixed pixels, the first mixed pixel (Mg+Cy) is highly sensitive to the blue narrowband light, so it is conceivable to produce an image (superficial image) of the blue narrowband light using the first mixed pixel signal, but the first mixed pixel is highly sensitive to the green narrowband light too. As for the green narrowband light, on the other hand, since the second mixed pixel (G+Ye) is highly sensitive to the green narrowband light, it is conceivable to produce an image (middle to deep image) of the green narrowband light using the second mixed pixel signal, but the second mixed pixel is slightly sensitive to the blue narrowband light too.

The use of the complementary color type imaging device has the advantages of high sensitivity and easy producibility of the primary color signal in the normal light observation. However, in the narrowband light observation, the complementary color type imaging device is inferior in color separability of a blue narrowband light component and a green narrowband light component. The superficial image and the middle to deep image are mixed, and the superficial blood vessels have low contrast. Therefore, it is desirable to improve the color separability in the narrowband light observation using the complementary color type imaging device.

SUMMARY OF THE INVENTION

An object of the present invention is to provide an endoscope system and a light source device that allow improvement in color separability in narrowband light observation using a complementary color type imaging device.

To achieve the above and other objects, an endoscope system according to the present invention includes a complementary color type imaging device and a lighting section. The complementary color type imaging device has a first mixed pixel and a second mixed pixel. Each of the first mixed pixel and the second mixed pixel senses both of first narrowband light and second narrowband light having a longer wavelength than the first narrowband light. A first mixed pixel signal is read from the first mixed pixel, and a second mixed pixel signal is read from the second mixed pixel. The lighting section has a light source device for simultaneously applying the first and second narrowband light to an observation object. The light amount ratio of the first narrowband light to the second narrowband light is set within a predetermined range based on an optimal light amount ratio. At the optimal light amount ratio, the proportion of a first narrowband light component within the first mixed pixel signal is equal to the proportion of a second narrowband light component within the second mixed pixel signal.

The complementary color type imaging device preferably has a matrix of at least four types of pixels for performing photoelectric conversion of light of different colors. Two types of the four types of pixels next to in a vertical scan direction compose the first mixed pixel. Other two types of the four types of pixels next to in the vertical scan direction compose the second mixed pixel.

The light amount ratio is preferably set at a value "Z" satisfying the following expression (a):

$$Z_0(1-\Delta) \leq Z \leq Z_0(1+\Delta) \tag{a}$$

wherein, $Z_0$ represents the optimal light amount ratio defined by $Z_0 = Z_1(R_1/R_2)^{1/2}$. $\Delta=0.5$. $R_1$ represents the ratio of a signal value of the first mixed pixel under independent application of only the second narrowband light to a signal value of the first mixed pixel under independent application of only the first narrowband light. $R_2$ represents the ratio of a signal value of the second mixed pixel under independent application of only the first narrowband light to a signal value of the second mixed pixel under independent application of only the second narrowband light. $Z_i$ represents the ratio of the light amount of the first narrowband light to the light amount of the second narrowband light in the independent application.

The ratio $R_1$ is preferably a value in which the average of the signal values of the first mixed pixels under independent application of only the second narrowband light is divided by the average of the signal values of the first mixed pixels under independent application of only the first narrowband light. The ratio $R_2$ is preferably a value in which the average of the signal values of the second mixed pixels under independent application of only the first narrowband light is divided by the average of the signal values of the second mixed pixels under independent application of only the second narrowband light.

The light amount ratio is preferably set at a value "Z" satisfying the following expression (b):

$$Z_0(1-\Delta) \leq Z < Z_0 \tag{b}$$

The light amount ratio is preferably set so as to be equal to the optimal light amount ratio.

It is preferable that a complementary color type endoscope having the complementary color type imaging device and a primary color type endoscope having a primary color type imaging device be detachably connected to the light source device.

It is preferable that the endoscope system further include a controller for controlling the light source device such that the light amount ratio is set at a larger value in a case where the complementary color type endoscope is connected to the light source device than in a case where the primary color type endoscope is connected to the light source device.

The controller preferably sets the light amount ratio at "1" in a case where the primary color type endoscope is connected to the light source device, while the controller preferably sets the light amount ratio at "Z" satisfying the expression (a) in a case where the complementary color type endoscope is connected to the light source device.

Each of the complementary color type endoscope and the primary color type endoscope preferably has information storage for storing specific information. The controller preferably reads out the specific information from the information storage of the complementary color type endoscope or the primary color type endoscope that is connected to the light source device, in order to judge the type of the connected endoscope.

The information storage of the complementary color type endoscope preferably stores the optimal light amount ratio. In a case where the complementary color type endoscope is connected to the light source device, the controller preferably determines the light amount ratio based on the optimal light amount ratio read out of the information storage.

The endoscope system preferably has a calibration mode for calculating the optimal light amount ratio under applying the first and second narrowband light independently from the light source device. The controller preferably stores the optimal light amount ratio calculated in the calibration mode to the information storage of the complementary color type endoscope connected to the light source device.

The light source device preferably includes a plurality of LEDs. The controller preferably sets the light amount ratio by regulating at least one of light emission intensity and light emission time of the plurality of LEDs.

The endoscope system preferably includes a corrector for correcting a signal value M1 of the first mixed pixel and a signal value M2 of the second mixed pixel on the basis of the following expressions (c) and (d):

$$M1' = M1 - K_2 \times M2 \tag{b}$$

$$M2' = M2 - K_1 \times M1 \tag{c}$$

wherein, $K_1$ represents the ratio of the signal value of the second mixed pixel to the signal value of the first mixed pixel under independent application of only the first narrowband light, $K_2$ represents the ratio of the signal value of the first mixed pixel to the signal value of the second mixed pixel under independent application of only the second narrowband light.

The complementary color type imaging device preferably has a complementary color type color separation filter of a complementary-color checkered-pattern color-difference line sequential method having color filter segments of cyan, magenta, yellow, and green. The first mixed pixel is preferably a combination of a magenta pixel and a cyan pixel, and the second mixed pixel is a combination of a green pixel and a yellow pixel. The first narrowband light preferably has a center wavelength in a blue or violet wavelength range, and the second narrowband light preferably has a center wavelength in a green wavelength range.

The endoscope system preferably includes a channel allocator that assigns the signal value of the first mixed pixel to a B channel and a G channel of an image display device, and assigns the signal value of the second mixed pixel to an R channel of the image display device, to display a special image.

The light amount ratio is preferably set at a value "Z" satisfying the following expression (e):

$$Z_0(1-\Delta) \leq Z < Z_0(1+\Delta) \quad (e)$$

wherein, $Z_0$ represents the optimal light amount ratio defined by $Z_0=(r_1/r_2)^{1/2}$. $\Delta=0.5$. $r_1$ is a value in which the sensitivity of the first mixed pixel to the first narrowband light is divided by the sensitivity of the first mixed pixel to the second narrowband light. $r_2$ is a value in which the sensitivity of the second mixed pixel to the second narrowband light is divided by the sensitivity of the second mixed pixel to the first narrowband light.

A light source device according to the present invention includes a light source and a light source controller. The light source simultaneously produces first narrowband light and second narrowband light having a longer wavelength than the first narrowband light and supplies the first and second narrowband light to an endoscope. The light source controller controls the light source. A complementary color type imaging device from which a first mixed pixel and a second mixed pixel are read out is connectable to the light source device. The first mixed pixel and the second mixed pixel sense both of the first narrowband light and the second narrowband light. The light amount ratio of the first narrowband light to the second narrowband light is set within a predetermined range based on an optimal light amount ratio at which the proportion of a first narrowband light component within a first mixed pixel signal is equal to the proportion of a second narrowband light component within a second mixed pixel signal.

According to the present invention, the light amount ratio of the first narrowband light to the second narrowband light is set within a predetermined range based on the optimal light amount ratio at which the proportion of the first narrowband light component within the first mixed pixel signal is equal to the proportion of the second narrowband light component within the second mixed pixel signal. Therefore, the color separability is improved.

BRIEF DESCRIPTION OF DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

Figure 1:
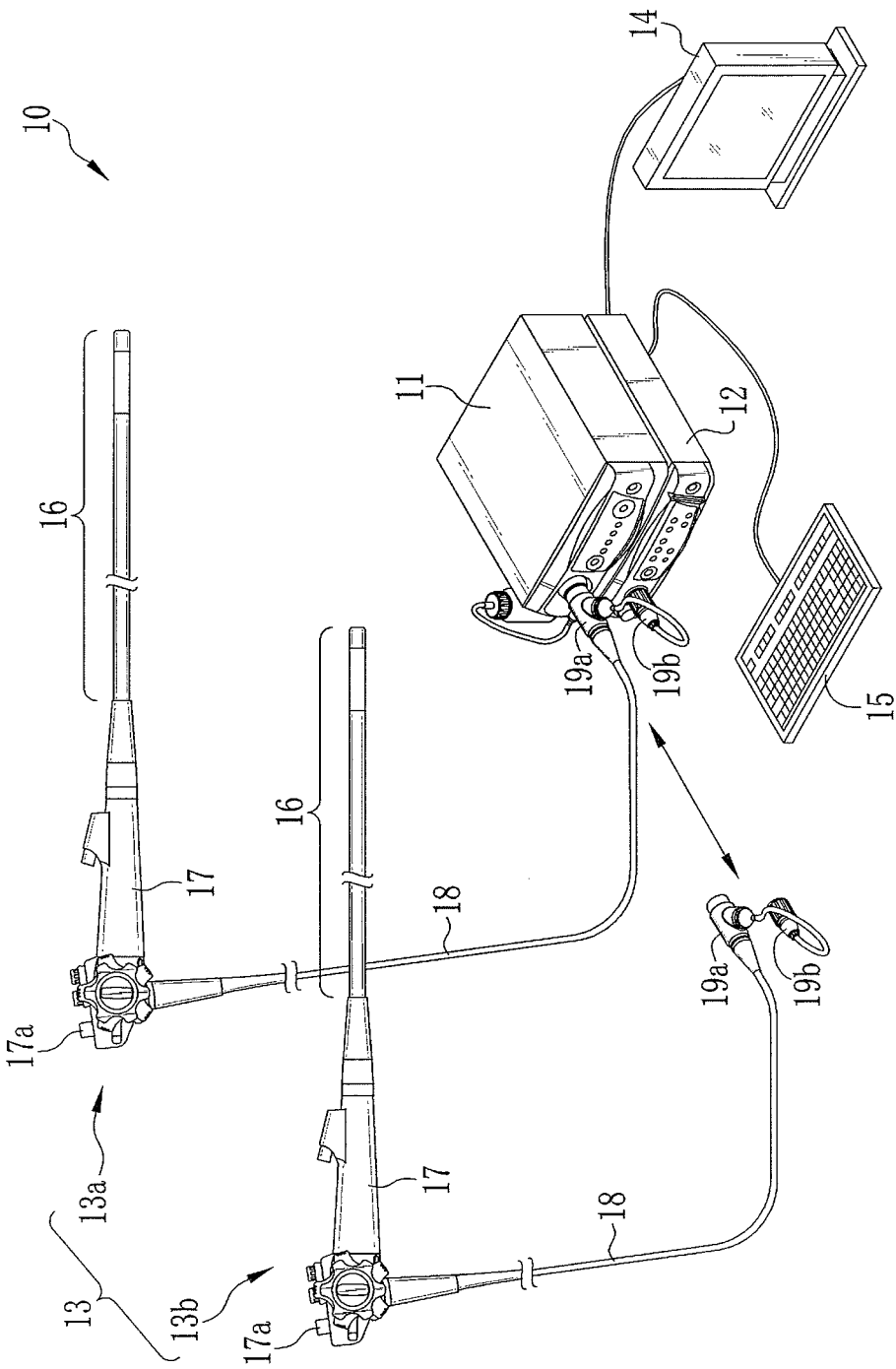
FIG. 1 is a schematic view of an endoscope system.

In FIG. 1, an endoscope system 10 is constituted of a light source device 11, a processor device 12, and electronic endoscopes 13 (hereinafter simply called endoscopes) detachably connected to the light source device 11 and the processor device 12. The light source device 11 produces illumination light and supplies the endoscope 13 with the illumination light. A distal end of the endoscope 13 is inserted into a human body cavity or the like to image the inside of the body cavity. The processor device 12 controls the imaging operation of the endoscope 13, and applies signal processing to an imaging signal obtained by the endoscope 13.

To the processor device 12, an image display device 14 and an input device 15 are connected. The image display device 14, being a liquid crystal display or the like, displays an image of an observation object inside the body cavity produced by the processor device 12. The input device 15, including a keyboard and a mouse, is used for inputting various types of information to the processor device 12.

Figure 2:
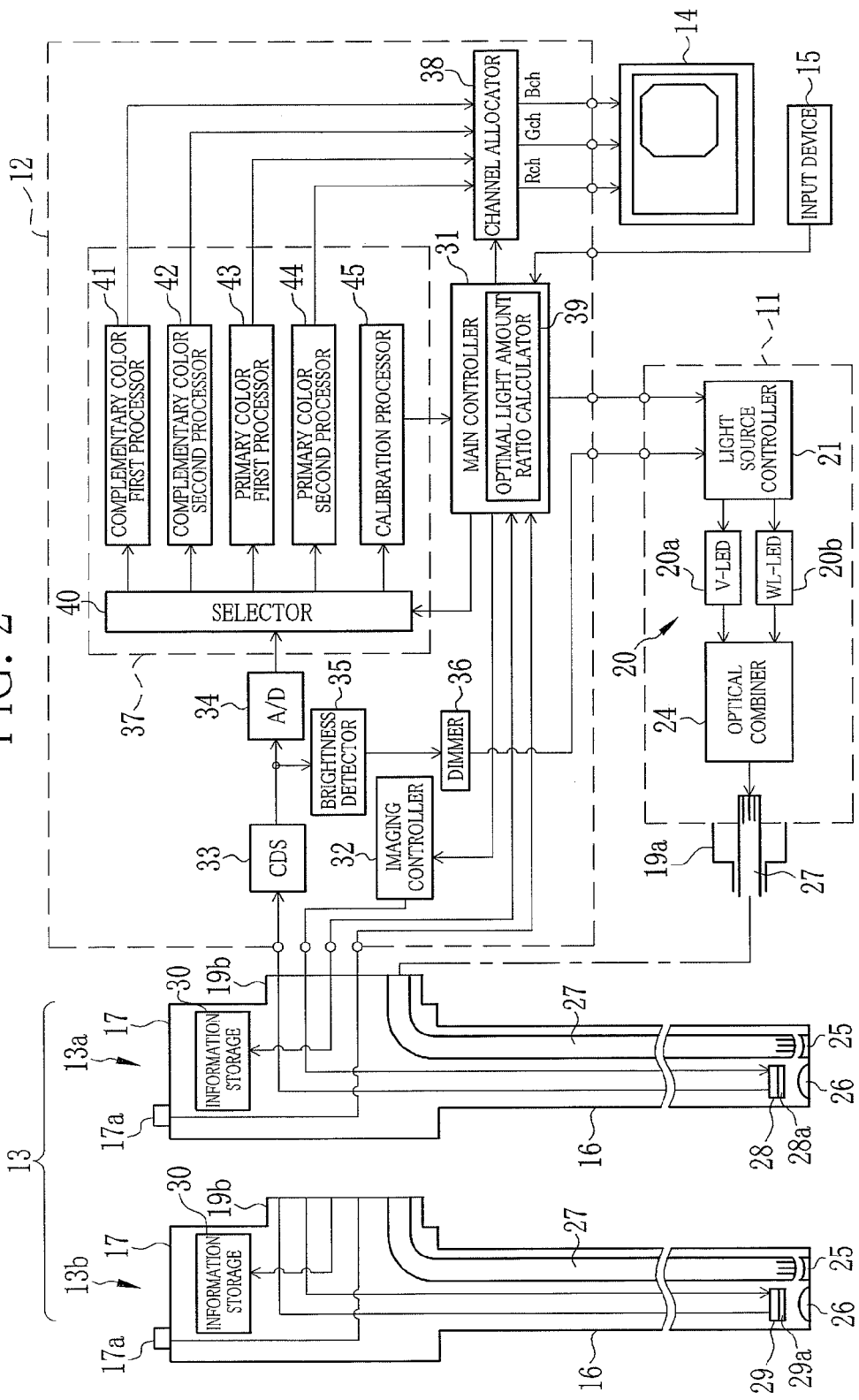
FIG. 2 is a block diagram of the endoscope system.

The endoscopes 13 include a complementary color type endoscope 13a having a complementary color type imaging device 28 (see FIG. 2) and a primary color type endoscope 13b having a primary color type imaging device 29 (see FIG. 2). Either of the complementary color type endoscope 13a and the primary color type endoscope 13b is connectable to the light source device 11 and the processor device 12. The complementary color type endoscope 13a and the primary color type endoscope 13b have identical structure except for the imaging device. Each endoscope 13a or 13b includes an insert section 16, a control handle unit 17, a universal cable 18, a light guide connector 19a, and a signal connector 19b.

The slender insert section 16 is introduced into the human body cavity or the like. The control handle unit 17 is coupled to a rear end of the insert section 16. The control handle unit 17 is provided with various switches, a bending operation dial, and the like. The various switches include a mode switch 17a for switching an operation mode.

The universal cable 18 extends from the control handle unit 17. The light guide connector 19a and the signal connector 19b are attached to an end of the universal cable 18. The light guide connector 19a is detachably connected to the light source device 11. The signal connector 19b is detachably connected to the processor device 12.

As an observation mode of the endoscope system 10, there are provided a normal light observation mode and a narrowband light observation mode. In the normal light observation mode, the observation object is imaged under irradiation with normal light (white light) having a wavelength band extending from the blue region to the red region, and a normal image is produced. In the narrowband light observation mode, the observation object is imaged under irradiation with narrowband light (violet narrowband light Vn and green narrowband light Gn, described later on) having a narrow wavelength band, and a narrowband light image is produced. Both of the complementary color type endoscope 13a and the primary color type endoscope 13b can carry out the normal light observation mode and the narrowband light observation mode.

The endoscope system 10 is switchable between the normal light observation mode and the narrowband light observation mode by operation of the mode switch 17a described above, but may be switched by operation of a foot switch (not shown) connected to the processor device 12, a button provided on a front panel of the processor device 12, the input device 15, or the like.

Figure 3:
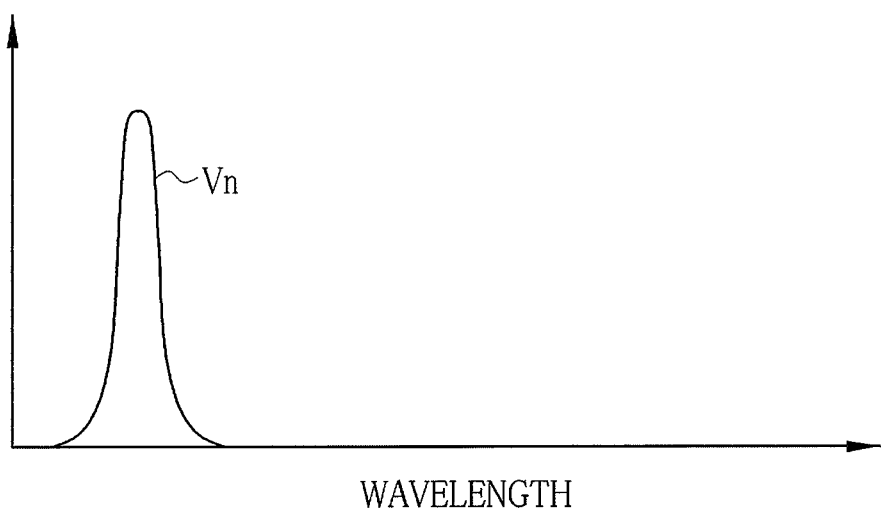
FIG. 3 is a graph showing an emission spectrum of violet narrowband light.
Figure 4:
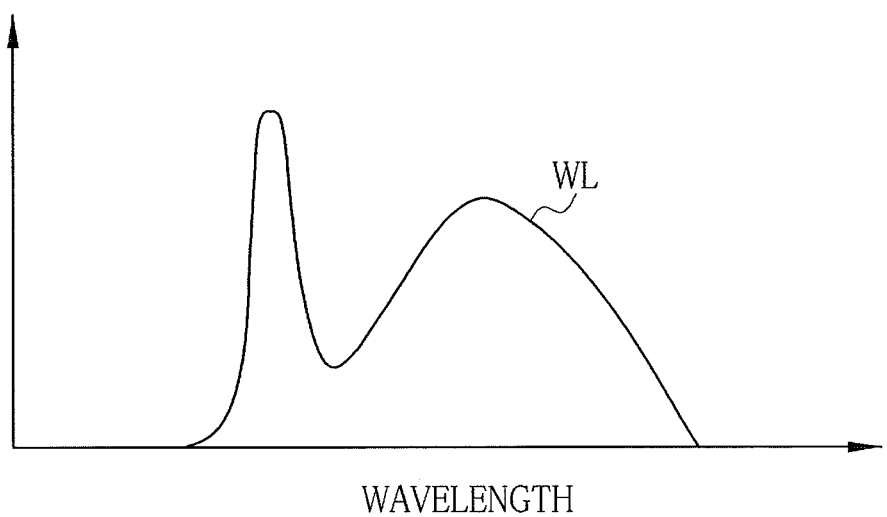
FIG. 4 is a graph showing an emission spectrum of normal light.

In FIG. 2, the light source device 11 has an LED light source 20 including a plurality of LEDs (light emitting diodes), a light source controller 21, and an optical combiner 24. The LED light source 20 includes a violet LED (V-LED) 20a and a white LED (WL-LED) 20b. Referring to FIG. 3, the V-LED 20a produces violet narrowband light Vn having a wavelength band of 380 to 440 nm. Referring to FIG. 4, the WL-LED 20b produces white light WL of a wide wavelength band. The light source controller 21 controls light emission from the V-LED 20a and the WL-LED 20b.

Figure 5:
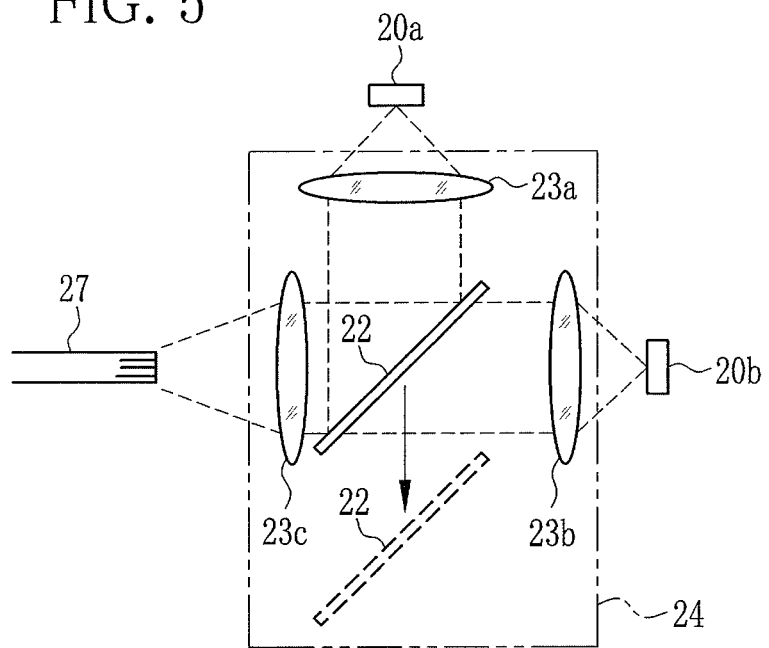
FIG. 5 is an explanatory view of the structure of an optical combiner.

As shown in FIG. 5, the optical combiner 24 has a dichroic mirror 22 and first to third lenses 23a to 23c. The first lens 23a is disposed in front of the LED 20a, and gathers and collimates the light emitted from the LED 20a. The second lens 23b is disposed in front of the LED 20b, and gathers and collimates the light emitted from the LED 20b. The V-LED 20a and the WL-LED 20b are disposed such that optical axes of the V-LED 20a and the WL-LED 20b are orthogonal to each other. The dichroic mirror 22 is situated at an intersection point of the optical axes.

Figure 6:
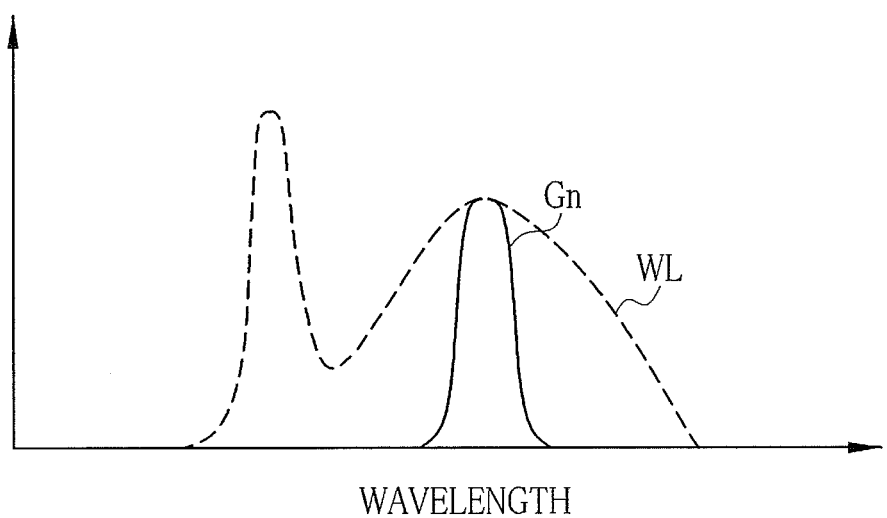
FIG. 6 is a graph showing an emission spectrum of green narrowband light.

The dichroic mirror 22 transmits light in a wavelength band of 530 nm or more and less than 550 nm, and reflects light in a wavelength of less than 530 nm or 550 nm or more, for example. Thus, the violet narrowband light Vn is reflected by the dichroic mirror 22 and gathered by the third lens 23c. On the other hand, apart of the white light WL is passed through the dichroic mirror 22, and gathered by the third lens 23c as green narrowband light Gn having a wavelength band of 530 to 550 nm, as shown in FIG. 6.

In the narrowband light observation mode, the V-LED 20a and the WL-LED 20b are simultaneously turned on. The violet narrowband light Vn and the green narrowband light Gn are combined (mixed) by the dichroic mirror 22 and gathered by the third lens 23c, and enter a light guide 27.

In the normal light observation mode, a shift mechanism (not shown) moves the dichroic mirror 22 out of the optical axis of the WL-LED 20b. Thus, in the normal light observation mode, the white light WL is directly incident upon the third lens 23c, and led into the light guide 27. Since the dichroic mirror 22 is retracted in the normal light observation mode, the violet narrowband light Vn emitted from the V-LED 20a is not incident upon the third lens 23c even if the dichroic mirror 22 reflects the violet narrowband light Vn. Thus, the V-LED 20a is preferably turned off, but there is no harm in turning on the V-LED 20a.

The center wavelength of the violet narrowband light Vn is approximately 405 nm at which hemoglobin has a high absorption coefficient in the visible region. The center wavelength of the green narrowband light Gn is approximately 540 nm at which hemoglobin has a high absorption coefficient in the green wavelength region. The green narrowband light Gn has a higher reflectance from a mucosa membrane than the violet narrowband light Vn.

The insert section 16 of the endoscope 13 has at its tip end a lighting window and an image capturing window provided next to each other. A lighting lens 25 is fitted into the lighting window. An objective lens 26 is fitted into the image capturing window. The light guide 27 extends through the endoscope 13, and one end of the light guide 27 is opposed to the lighting lens 25. The other end of the light guide 27 is provided with the light guide connector 19a. In a state of fitting the light guide connector 19a to the light source device 11, the other end of the light guide 27 is inserted into the light source device 11.

The lighting lens 25 gathers the light that is transmitted from the light source device 11 through the light guide 27 and ejected from the light guide 27, and applies the light to the observation object inside the body cavity. The objective lens 26 gathers reflected light from living body tissue and the like of the observation object, and forms an optical image. In an image forming position of the objective lens 26, an imaging device (the complementary color type imaging device 28 in the case of the complementary color type endoscope 13a, the primary color type imaging device 29 in the case of the primary color type endoscope 13b) is disposed to capture the optical image and produce the imaging signal. The complementary color type imaging device 28 and the primary color type imaging device 29 are CCD (charge coupled device) image sensors.

Figure 7:
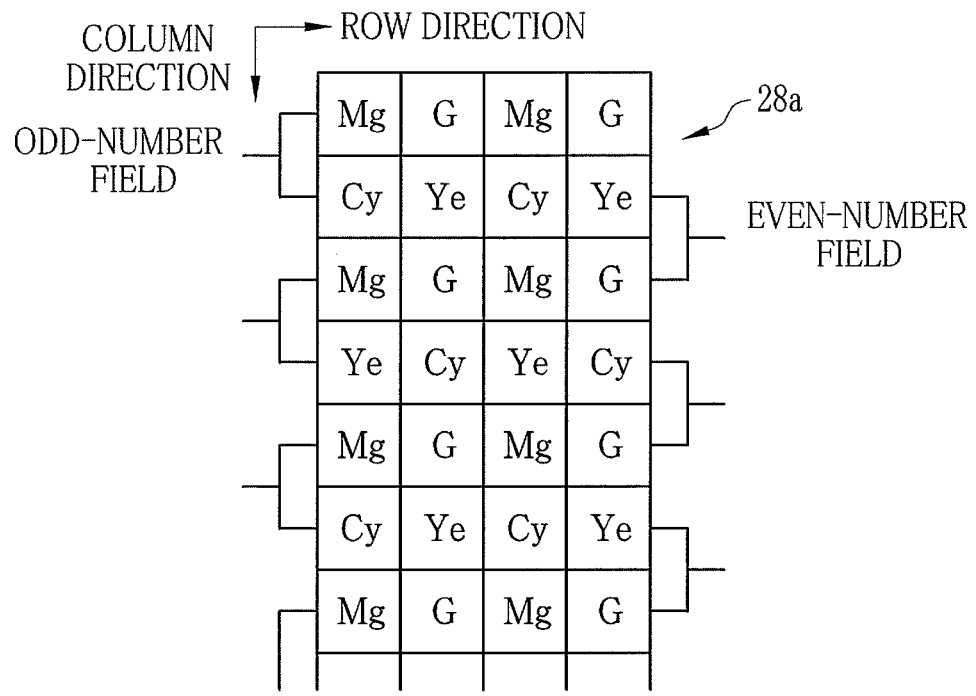
FIG. 7 is a schematic view of a complementary color type color separation filter.

The complementary color type imaging device 28 is provided at its imaging surface with a complementary color type color separation filter 28a to perform optical color separation of the optical image on a pixel-by-pixel basis. As shown in FIG. 7, this complementary color type color separation filter 28a has four types of color filter segments of magenta (Mg), green (G), cyan (Cy), and yellow (Ye), and one color filter segment is provided for each pixel. Accordingly, the complementary color type imaging device 28 has four types of pixels of Mg, G, Cy, and Ye. The Mg pixels and the G pixels are alternately arranged in odd-number rows, and the Cy pixels and the Ye pixels are alternately arranged in even-number rows, such that the Mg pixel, the Cy pixel, the Mg pixel, the Ye pixel, . . . are arranged in this order in odd-number columns, and the G pixel, the Ye pixel, the G pixel, the Cy pixel . . . are arranged in this order in even-number columns. This color filter pattern is referred to as a complementary-color checkered-pattern color-difference line sequential method. A row direction refers to a horizontal scan direction, and a column direction refers to a vertical scan direction.

Figure 8:
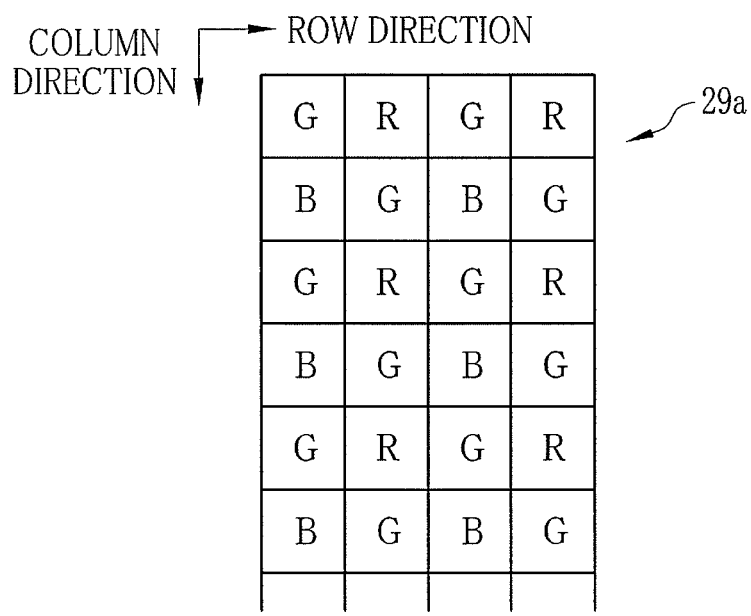
FIG. 8 is a schematic view of a primary color type color separation filter.

The primary color type imaging device 29 is provided at its imaging surface with a primary color type color separation filter 29a. As shown in FIG. 8, this primary color type color separation filter 29a has three types of color filter segments of red (R), green (G), and blue (B), which are three primary colors of an additive color process. One color filter segment is provided for each pixel. Accordingly, the primary color type imaging device 29 has three types of pixels of R, G, and B. The G pixels and the B pixels are alternately arranged in odd-number columns, and the R pixels and the G pixels are alternately arranged in even-number columns. The G pixels and the R pixels are alternately arranged in odd-number rows, and the B pixels and the G pixels are alternately arranged in even-number rows. This color filter pattern is referred to as a primary color Bayer pattern.

The endoscope 13 includes information storage 30 composed of a non-volatile memory such as a flash memory. The information storage 30 stores specific information (the color filter pattern and the pixel number of the imaging device) and the like of the endoscope 13.

The processor device 12 has a main controller 31, an imaging controller 32, a correlated double sampling (CDS) circuit 33, an A/D converter 34, a brightness detector 35, a dimmer 36, a signal processing unit 37, and a channel allocator 38.

The main controller 31 controls each part of the processor device 12 and the light source device 11. Upon connecting the endoscope 13 to the light source device 11 and the processor device 12, the main controller 31 reads the specific information of the endoscope 13 from the information storage 30, and judges whether the connected endoscope 13 is the complementary color type endoscope 13a or the primary color type endoscope 13b. The imaging controller 32 actuates the imaging device (complementary color type imaging device 28 or the primary color type imaging device 29) in accordance with the type of the endoscope 13 judged by the main controller 31.

Figure 9:
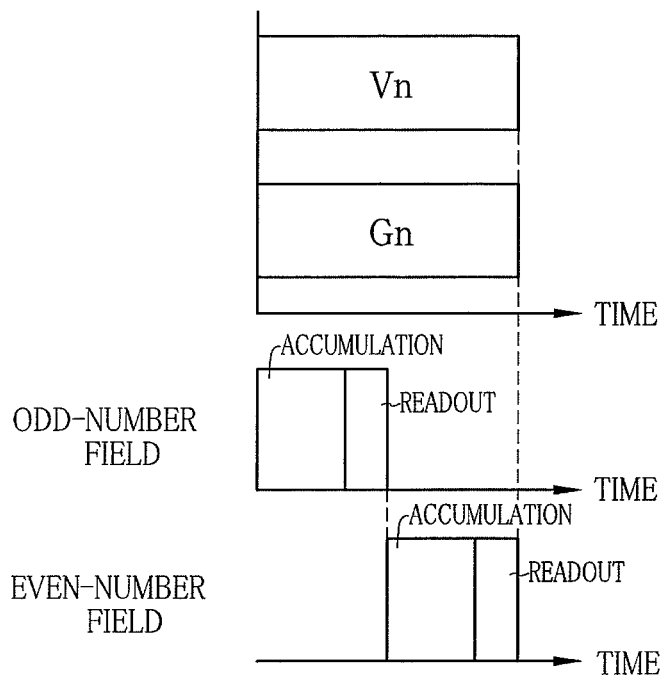
FIG. 9 is a timing chart of light sources and a complementary color type imaging device in a narrowband light observation mode.

In the case of the complementary color type imaging device 28, the imaging controller 32 drives the complementary color type imaging device 28 by a field readout method in synchronization with emission timing of the light source device 11. To be more specific, according to the field readout method, pixel signals of two pixels adjoining in the column direction (vertical scan direction) are read out in a mixed (added) manner in reading each of an odd-number field and an even-number field (see FIG. 7). The mixture of the pixel signals is performed in a horizontal transfer path (not shown) of the CCD image sensor by using the pixel signals of two rows. FIG. 9 shows a timing chart of the narrowband light observation mode. A timing chart of the normal light observation mode is the same as that of the narrowband light observation mode, except that the illumination light is the white light WL.

Figure 10:
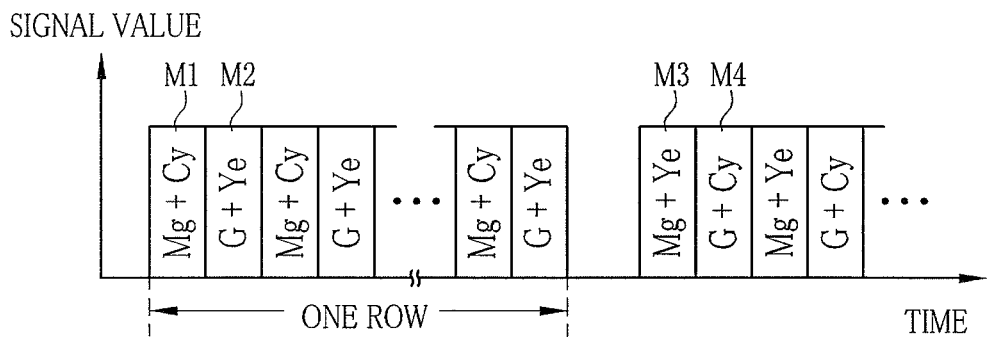
FIG. 10 is an explanatory view of output signals from the complementary color type imaging device.

According to the field readout method, as shown in FIG. 10, a mixed pixel signal (hereinafter called a first mixed pixel signal) M1 of the Mg pixel and the Cy pixel, a mixed pixel signal (hereinafter called a second mixed pixel signal) M2 of the G pixel and the Ye pixel, a mixed pixel signal (hereinafter called a third mixed pixel signal) M3 of the Mg pixel and the Ye pixel, and a mixed pixel signal (hereinafter called a fourth mixed pixel signal) M4 of the G pixel and the Cy pixel are read out from the complementary color type imaging device 28 in each of the odd-number field and the even-number field.

Figure 11:
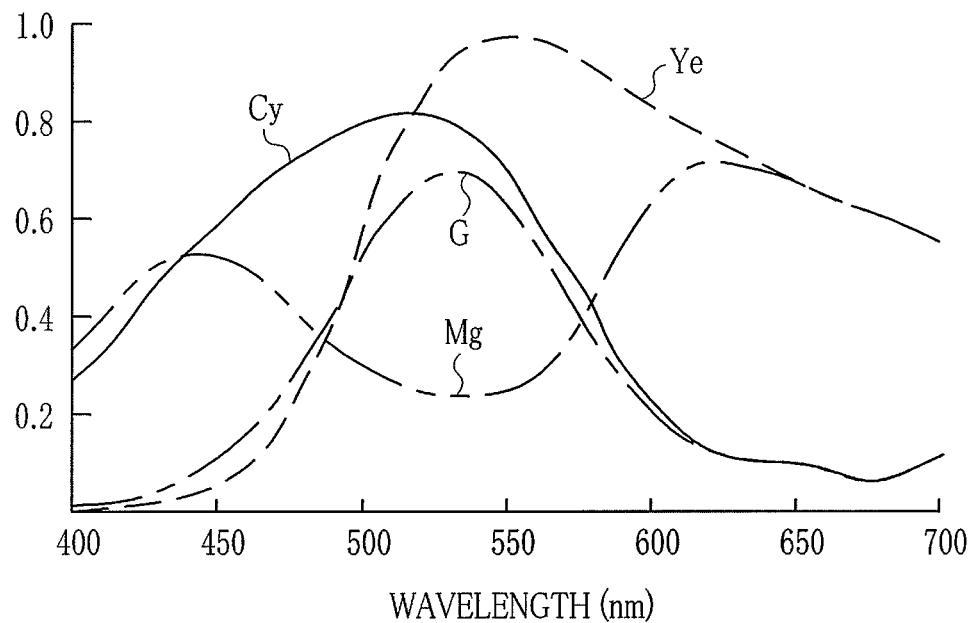
FIG. 11 is a graph of spectral sensitivity characteristics of the complementary color type imaging device.
Figure 12:
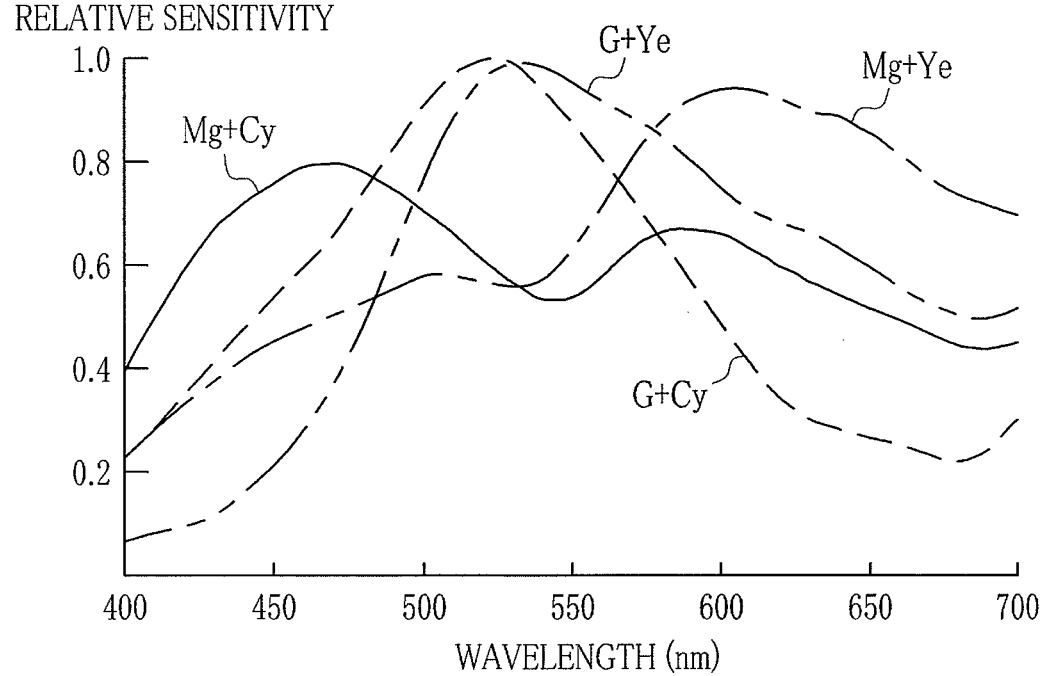
FIG. 12 is a graph of spectral sensitivity characteristics of first to fourth mixed pixels.

Since the pixels of the complementary color type imaging device 28 have spectral sensitivity characteristics as shown in FIG. 11, for example, in accordance with the color filter segments provided thereto, the mixed pixels have spectral sensitivity characteristics as shown in FIG. 12, for example. As is apparent from the spectral sensitivity characteristics, out of the first to fourth mixed pixels, the first mixed pixel (Mg+Cy) is the most sensitive to the violet narrowband light Vn (a center wavelength of 405 nm), and the second mixed pixel (G+Ye) is the most sensitive to the green narrowband light Gn (a center wavelength of 540 nm). However, the first mixed pixel (Mg+Cy) has high sensitivity to the green narrowband light Gn too. The second mixed pixel (G+Ye) has a little sensitivity to the violet narrowband light Vn.

In the narrowband light observation mode, the violet narrowband light Vn is imaged based on the first mixed pixel signal M1, and the green narrowband light Gn is imaged based on the second mixed pixel signal M2. On the other hand, in the normal light observation mode, imaging is performed by using all of the first to fourth mixed pixel signals M1 to M4.

In the case of the primary color type imaging device 29, the imaging controller 32 drives the primary color type imaging device 29 by a well-known progressive readout method in synchronization with emission timing of the light source device 11. According to the progressive readout method, the pixel signals of one frame are read out sequentially and individually on a row-by-row basis, without mixing the pixel signals.

A signal outputted from the complementary color type imaging device 28 or the primary color type imaging device 29 is inputted to the CDS circuit 33. The CDS circuit 33 applies correlated double sampling to the inputted signal to remove a noise component occurring in the CCD image sensor. The signal, after the noise removal by the CDS circuit 33, is inputted to the A/D converter 34 and the brightness detector 35. The A/D converter 34 converts the signal inputted from the CDS circuit 33 into a digital signal, and inputs the digital signal to the signal processing unit 37.

The brightness detector 35 detects as brightness (average luminance of the signal) an average value of G signals, in general, based on the signal inputted from the CDS circuit 33. The dimmer 36 produces a dimming signal, which represents the difference between a brightness signal detected by the brightness detector 35 and standard brightness (a target dimming value). This dimming signal is inputted to the light source controller 21. The light source controller 21 adjusts the light emission amount of the LED light source 20 so as to obtain the standard brightness.

Upon receiving a mode switching signal issued by the operation of the mode switch 17a of the endoscope 13, the main controller 31 switches a light emission method of the light source device 11 and a signal processing method of the signal processing unit 37 in accordance with the received mode switching signal.

In the narrowband light observation mode, the main controller 31 controls the light source controller 21 in accordance with the type of the endoscope 13 defined by the specific information read out of the information storage 30 so as to change the light emission intensity of the V-LED 20a and the WL-LED 20b. More specifically, in the case of the primary color type endoscope 13b, the main controller 31 controls the light source controller 21 so as to substantially equalize the light amounts of the violet narrowband light Vn and the green narrowband light Gn applied from the primary color type endoscope 13b to the observation object.

On the other hand, in the case of the complementary color type endoscope 13a, the main controller 31 controls the light source controller 21 such that the light amount ratio Z (Z=X/Y) of the light amount X of the violet narrowband light Vn to the light amount Y of the green narrowband light Gn applied from the complementary color type endoscope 13a to the observation object satisfies the following expression (1). This light amount ratio Z is at least larger than the light amount ratio in the case of the primary color type endoscope 13b.

$$Z_0(1-\Delta) \leq Z \leq Z_0(1+\Delta) \quad (1)$$

Wherein, $Z_0$ represents a light amount ratio that is optimal as the above light amount ratio Z, and a value defined by an expression (2). This optimal light amount ratio $Z_0$ increases and equalizes both of the proportion of a violet narrowband light Vn component within the first mixed pixel signal M1 and the proportion of a green narrowband light Gn component within the second mixed pixel signal M2 obtained in the narrowband light observation mode (in other words, most improves color separability), though details will be described later.

$$Z_0 = Z_i \sqrt{R_1/R_2} \quad (2)$$

$R_1$ and $R_2$ are obtained based on values of the first and second mixed pixel signals in the case of independently applying (by time-sharing application) the violet narrowband light Vn and the green narrowband light Gn from the light source 11. $R_1$ represents the ratio (M1g/M1v) of a first mixed pixel signal M1g obtained under independent application of only the green narrowband light Gn to a first mixed pixel signal M1v obtained under independent application of only the violet narrowband light Vn. $R_2$ represents the ratio (M2v/M2g) of a second mixed pixel signal M2v obtained under independent application of only the violet narrowband light Vn to a second mixed pixel signal M2g obtained under independent application of only the green narrowband light Gn. $Z_i$ represents the ratio ($X_i/Y_i$) of the light amount $X_i$ of the violet narrowband light Vn to the light amount $Y_i$ of the green narrowband light Gn in the independent application.

Each of the first mixed pixel signals M1v and M1g is preferably an average of a plurality of first mixed pixel signal values (for example, an average of all the first mixed pixel signal values of the odd-number field and the even-number field). Similarly, each of the second mixed pixel signals M2g and M2v is preferably an average of a plurality of second mixed pixel signal values (for example, an average of all the second mixed pixel signal values of the odd-number field and the even-number field).

In the expression (1), $\Delta$ represents a value that defines a margin of the optimal light amount ratio $Z_0$ in determining the light amount ratio Z, and $\Delta=0.5$ in this embodiment. Especially, $Z=Z_0$ preferably holds true in order to most increase the color separability.

To obtain this optimal light amount ratio $Z_0$, in a final test process or the like in the course of manufacturing the endoscope system 10, the violet narrowband light Vn and the green narrowband light Gn are independently emitted (by time-sharing application) from the light source device 11 at a predetermined light amount ratio $Z_i$ (for example, $Z_i=1$), and the first and second mixed pixel signals are obtained by the complementary color type imaging device 28, and the optimal light amount ratio $Z_0$ is calculated from the expression (2). The optimal light amount ratio $Z_0$ obtained in the course of manufacturing is recorded to the image storage 30 of the complementary color type endoscope 13a.

Provided that the complementary color type endoscope 13a is connected to the light source device 11 and the processor device 12 and the narrowband light observation mode is chosen by operation of the mode switch 17a, the main controller 31 reads out the optimal light amount ratio $Z_0$ stored in the information storage 30 of the complementary color type endoscope 13a. The main controller 31 controls the light source controller 21 to set the light emission intensity of the V-LED 20a and the WL-LED 20b by intensity modulation, such that the complementary color type endoscope 13a emits the violet narrowband light Vn and the green narrowband light Gn at the light amount ratio Z satisfying the expression (1).

Figure 13:
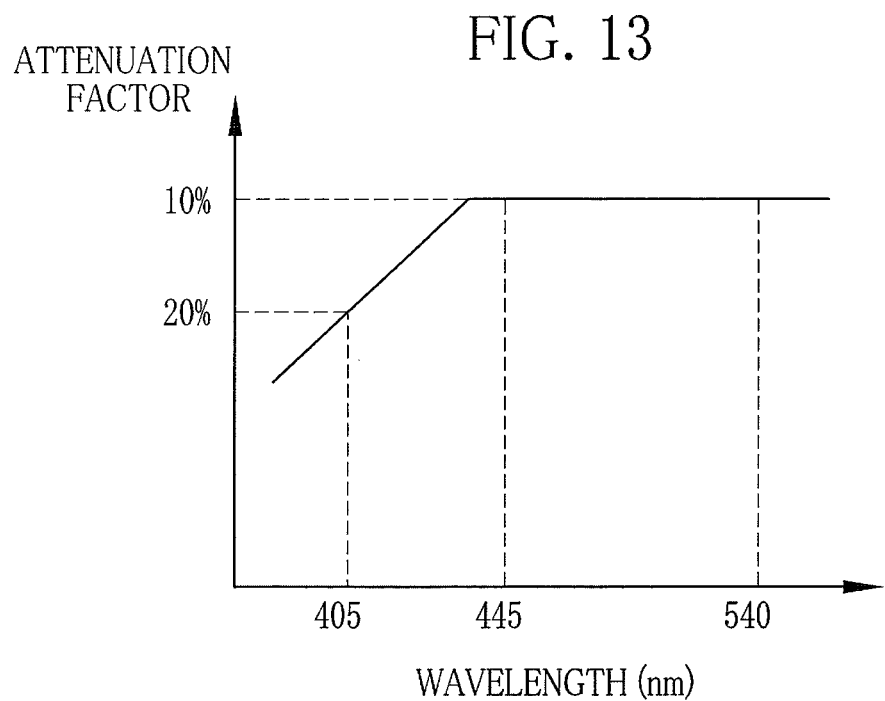
FIG. 13 is a graph of a spectral attenuation characteristic of a light guide.

The above light guide 27 has a spectral attenuation characteristic as shown in FIG. 13. An attenuation factor of propagating light is increased in a short wavelength range of approximately 440 nm or less. Thus, the violet narrowband light Vn emitted from the light source device 11 attenuates more strongly than the green narrowband light Gn in the light guide 27 of the complementary color type endoscope 13a. As a result, since the light emission intensity ratio between the V-LED 20a and the WL-LED 20b is not equal to the light amount ratio Z between the violet narrowband light Vn and the green narrowband light Gn emitted from the complimentary color type endoscope 13a, the main controller 31 determines the light emission intensity of the V-LED 20a and the WL-LED 20b in consideration of the spectral attenuation factor of the light guide 27. For example, the relation between the light emission intensity ratio of the V-LED 20a and the WL-LED 20b and the light amount ratio Z of the violet narrowband light Vn and the green narrowband light Gn emitted from the complementary color type endoscope 13a is measured in advance and put into a table. The V-LED 20a and the WL-LED 20b may be controlled based on this table.

Figure 14:
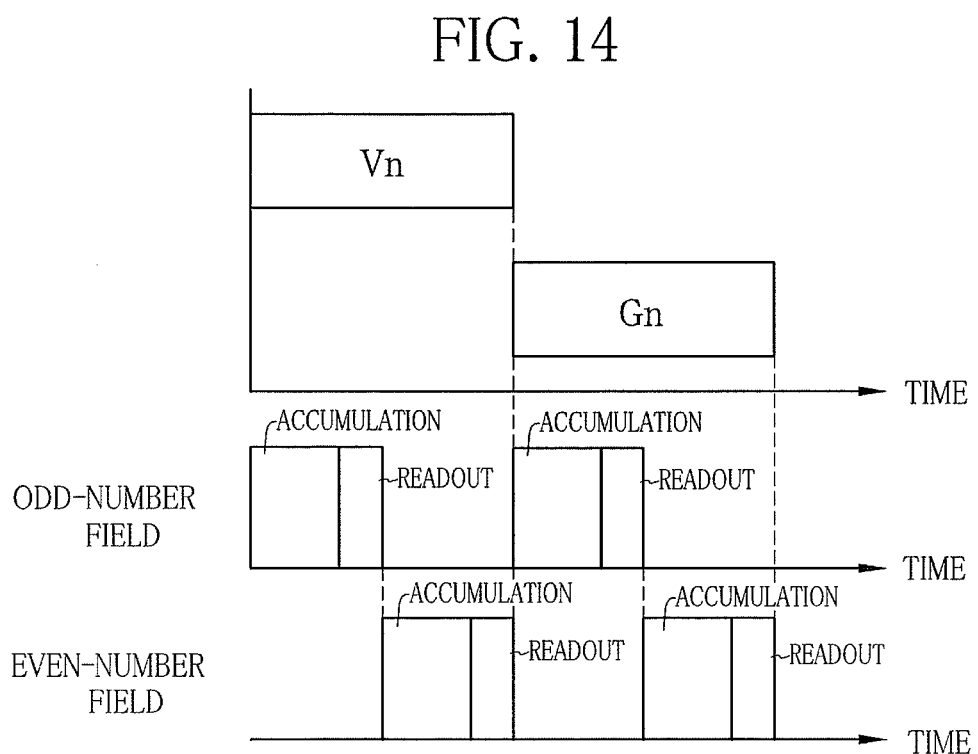
FIG. 14 is a timing chart of the light sources and the complementary color type imaging device in a calibration mode.

The endoscope system 10 has a calibration mode for allowing recalculation of the optimal light amount ratio $Z_0$ after the completion of the manufacture as a product. The calibration mode is chosen by operation of the input device 15 or the like. In the calibration mode, the main controller 31 turns on the V-LED 20a and the WL-LED 20b independently. Thus, as shown in FIG. 14, the violet narrowband light Vn and the green narrowband light Gn are applied in a time sharing manner, and the complementary color type imaging device 28 is driven in synchronization with emission timing.

In the calibration mode, the light amount ratio Z that has been set in the light source controller 21 is used as the light amount ratio $Z_i$ between the violet narrowband light Vn and the green narrowband light Gn. The main controller 31 includes an optimal light amount ratio calculator 39. The optimal light amount ratio calculator 39 calculates the optimal light amount ratio $Z_0$ by the expression (2). If the set light amount ratio Z is appropriate, $(R_1/R_2)^{1/2}$ becomes approximately "1" in the expression (2) and $Z_0 \cong Z_i$ holds true, so there is no need for modifying the set light amount ratio Z. Thus, the main controller 31 adjusts the light amount ratio Z by using the value of $(R_1/R_2)^{1/2}$ as a correction coefficient of the set light amount ratio Z.

The signal processing unit 37 includes a selector 40, a complementary color first processor 41, a complementary color second processor 42, a primary color first processor 43, a primary color second processor 44, and a calibration processor 45. The selector 40 chooses one of the processors 41 to 45 in accordance with the type and the operation mode of the endoscope 13 judged by the main controller 31.

The calibration processor 45 is chosen in the above calibration mode. In the calibration mode, a signal outputted from the complementary color type imaging device 28 is inputted to the signal processing unit 37 through the CDS circuit 33 and the A/D converter 34, and sent to the calibration processor 45 via the selector 40. The calibration processor 45 extracts the above first mixed pixel signals M1v and M1g and the second mixed pixel signals M2g and M2v from the input signal. The calibration processor 45 calculates an average of each signal value, and inputs the averages to the optimal light amount ratio calculator 39 of the main controller 31. The optimal light amount ratio calculator 39 calculates the optimal light amount ratio $Z_0$ from the signal values inputted from the calibration processor 45.

After performing the calibration, the main controller 31 deletes the optimal light amount ratio $Z_0$ that has been stored in the information storage 30 of the complementary color type endoscope 13a, and replaces it with the optimal light amount ratio $Z_0$ that is newly calculated by the optimal light amount ratio calculator 39.

The complementary color first processor 41 is chosen in a case where the endoscope 13 is of the complementary color type and the observation mode is the normal light observation mode. To the complementary color first processor 41, the first to fourth mixed pixel signals M1 to M4 (see FIG. 10) are inputted from the complementary color type imaging deice 28. The complementary color first processor 41 produces a luminance signal Y and color difference signals Cr and Cb by performing a well-known Y/C conversion used in the complementary-color checkered-pattern color-difference line sequential method, and then converts the luminance signal Y and the color difference signals Cr and Cb into the RGB signal by a matrix operation. This RGB signal is sent to the channel allocator 38. More specifically, the luminance signal Y and the color difference signals Cr and Cb are calculated by addition and subtraction of the first mixed pixel signal M1 and the second mixed pixel signal M2 next to each other in the row direction and addition and subtraction of the third mixed pixel signal M3 and the fourth mixed pixel signal M4 next to each other in the row direction.

Figure 15:
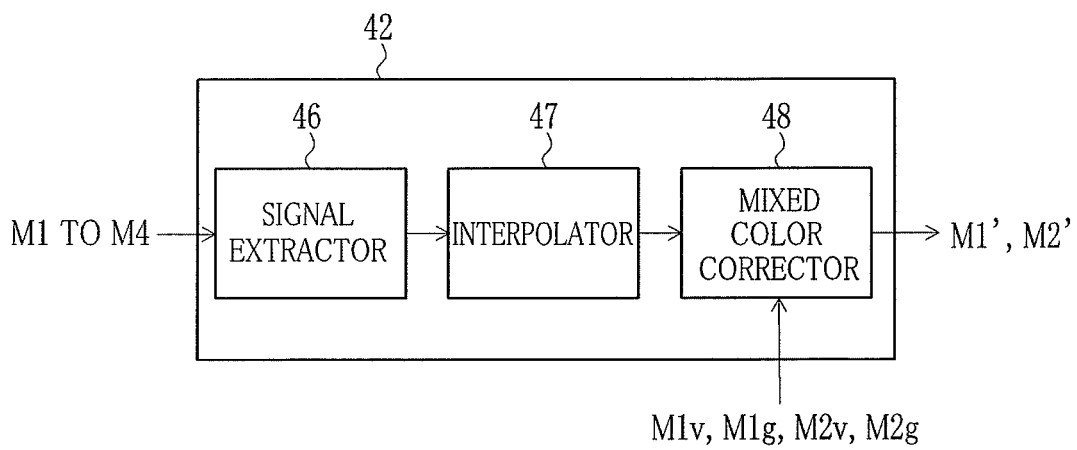
FIG. 15 is a block diagram of a complementary color first processor.

The complementary color second processor 42 is chosen in a case where the endoscope 13 is of the complementary color type and the observation mode is the narrowband light observation mode. As shown in FIG. 15, the complementary color second processor 42 has a signal extractor 46, an interpolator 47, and a mixed color corrector 48.

The signal extractor 46 extracts only the first and second mixed pixel signals M1 and M2 out of the first to fourth mixed pixel signals M1 to M4 inputted from the complementary color type imaging device 28, and inputs the first and second mixed pixel signals M1 and M2 to the interpolator 47. The interpolator 47 performs a well-known pixel interpolation processing, to produce two signals of the first and second mixed pixel signals M1 and M2 in the position of each mixed pixel. The mixed color corrector 48 performs mixed color correction processing by using the following expression (3):

$$\begin{pmatrix} M1' \\ M2' \end{pmatrix} = \begin{pmatrix} 1 & -K_2 \\ -K_1 & 1 \end{pmatrix} \begin{pmatrix} M1 \\ M2 \end{pmatrix} \quad (3)$$

Wherein, $K_1$ represents the ratio (M2v/M1v) of the second mixed pixel signal M2v to the first mixed pixel signal M1v obtained in independent application of only the violet narrowband light Vn. $K_2$ represents the ratio (M1g/M2g) of the first mixed pixel signal M1g to the second mixed pixel signal M2g obtained in independent application of only the green narrowband light Gn.

The mixed color corrector 48 calculates the correction coefficients $K_1$ and $K_2$ with the use of the first mixed pixel signals M1v and M1g and the second mixed pixel signals M2g and M2v obtained by the calibration processor 45 in the above calibration mode. The mixed color corrector 48 keeps holding the calculated correction coefficients $K_1$ and $K_2$ until the calibration is performed again.

The correction coefficients $K_1$ and $K_2$ may be obtained in the course of manufacture and stored to the information storage 30 of the complementary color type endoscope 13a, and the main controller 31 may obtain the correction coefficients $K_1$ and $K_2$ from the information storage 30 at the time when the complementary color type endoscope 13a is connected to the light source device 11 and the processor device 12. Furthermore, if the calibration is performed, the correction coefficients $K_1$ and $K_2$ stored in the information storage 30 of the complementary color type endoscope 13a are preferably deleted and replaced with the correction coefficients $K_1$ and $K_2$ newly calculated by the mixed color corrector 48.

The mixed color correction processing according to the expression (3) lowers a mixed color component (a green narrowband light Gn component in the first mixed pixel signal M1 and a violet narrowband light Vn component in the second mixed pixel signal M2). The first and second mixed pixel signals M1' and M2' after the mixed color correction are sent to the channel allocator 38.

The primary color first processor 43 is chosen in a case where the endoscope 13 is of the primary color type and the observation mode is the normal light observation mode. To the primary color first processor 43, the RGB signal is inputted from the primary color type imaging device 29. In this RGB signal, one of R, G, and B signals is assigned to each pixel. The primary color first processor 43 produces three signals of R, G, and B for each pixel by performing well-known pixel interpolation processing. The RGB signals produced by the pixel interpolation processing are sent to the channel allocator 38.

The primary color second processor 44 is chosen in a case where the endoscope 13 is of the primary color type and the observation mode is the narrowband light observation mode. To the primary color second processor 44, the RGB signal is inputted from the primary color type imaging device 29. The primary color second processor 44 extracts a B signal for sensing the violet narrowband light Vn and a G signal for sensing the green narrowband light Gn, and produces a B signal and a G signal of each pixel by applying the pixel interpolation processing as with above. The B signal and the G signal are sent to the channel allocator 38.

In the normal light observation mode, the channel allocator 38 receives the RGB signals irrespective of the type of the endoscope 13, and hence allocates the R, G, and B signals to an R channel, a G channel, and a B channel of the image display device 14, respectively. Therefore, the normal image, that is, an image of the observation object irradiated with the normal light is displayed on the image display device 14.

In a case where the endoscope 13 is of the complementary color type and the narrowband light observation mode is chosen, the channel allocator 38 assigns the first and second mixed pixel signals M1' and M2' inputted from the complementary color second processor 42 to the channels of the image display device 14 as indicated by the following expression (4):

$$\begin{pmatrix} Rch \\ Gch \\ Bch \end{pmatrix} = \begin{pmatrix} 0 & 1 \\ 1 & 0 \\ 1 & 0 \end{pmatrix} \begin{pmatrix} M1' \\ M2' \end{pmatrix} \quad (4)$$

Therefore, an image of the observation object irradiated with the violet narrowband light Vn and the green narrowband light Gn is displayed as the special image on the image display device 14. Since the expression (4) assigns the first mixed pixel signal M1' corresponding to the violet narrowband light Vn to the two channels, the special image is such an image in which the structure of the superficial blood vessels (blood capillary) and the like in the vicinity of the surface of a living body is easily visible. Note that, the first and second mixed pixel signals M1' and M2' may be weighted by coefficients other than "0" or "1" in assignment to the channels.

Furthermore, provided that the endoscope 13 is of the primary color type and the narrowband light observation mode is chosen, the channel allocator 38 assigns the B signal and the G signal inputted from the primary color second processor 44 to the channels of the image display device 14 as indicated by the following expression (5):

$$\begin{pmatrix} Rch \\ Gch \\ Bch \end{pmatrix} = \begin{pmatrix} 0 & 1 \\ 1 & 0 \\ 1 & 0 \end{pmatrix} \begin{pmatrix} B \\ G \end{pmatrix} \quad (5)$$

Thus, an image of the observation object irradiated with the violet narrowband light Vn and the green narrowband light Gn is displayed as the special image on the image display device 14. This special image is such an image in which the structure of the superficial blood vessels and the like in the vicinity of the surface of the living body is easily visible. In a like manner, the B signal and the G signal may be weighted by coefficients other than "0" or "1" in assignment to the channels.

Next, a method for obtaining the expression (2), which defines the optimal light amount ratio $Z_0$, will be described. The first and second mixed pixel signals M1 and M2 are represented by the following expression (6). In this expression, "X" and "Y" represent the light amounts of the violet narrowband light Vn and the green narrowband light Gn, respectively, simultaneously applied from the complementary color type endoscope 13a to the observation object. "$a_1$" represents average sensitivity of the first mixed pixels (Mg+Cy) to the violet narrowband light Vn. "$b_1$" represents average sensitivity of the first mixed pixels (Mg+Cy) to the green narrowband light Gn. "$a_2$" represents average sensitivity of the second mixed pixels (G+Ye) to the green narrowband light Gn. "$b_2$" represents average sensitivity of the second mixed pixels (G+Ye) to the violet narrowband light Vn. The average sensitivity refers to an average of sensitivity in the wavelength band of each type of narrowband light.

$$\begin{pmatrix} M1 \\ M2 \end{pmatrix} = \begin{pmatrix} a_1 & b_1 \\ b_2 & a_2 \end{pmatrix} \begin{pmatrix} X \\ Y \end{pmatrix} \quad (6)$$

The following expression (7) represents the proportion P1 of the violet narrowband light Vn component within the first mixed pixel signal M1. The following expression (8) represents the proportion P2 of the green narrowband light Gn component within the second mixed pixel signal M2.

$$P1 = \frac{a_1 X}{a_1 X + b_1 Y} = \frac{r_1 Z}{r_1 Z + 1} \quad (7)$$

$$P2 = \frac{a_2 Y}{b_2 X + a_2 Y} = \frac{r_2}{Z + r_2} \quad (8)$$

Wherein, $Z=X/Y$, $r_1=a_1/b_1$, and $r_2=a_2/b_2$ hold true by definition. "Z" is the light amount ratio Z, as described above. "$r_1$" is the ratio between the sensitivity of the first mixed pixel (Mg+Cy) to the violet narrowband light Vn and the sensitivity of the first mixed pixel (Mg+Cy) to the green narrowband light Gn. "$r_2$" is the ratio between the sensitivity of the second mixed pixel (G+Ye) to the green narrowband light Gn and the sensitivity of the second mixed pixel (G+Ye) to the violet narrowband light Vn.

Figure 16:
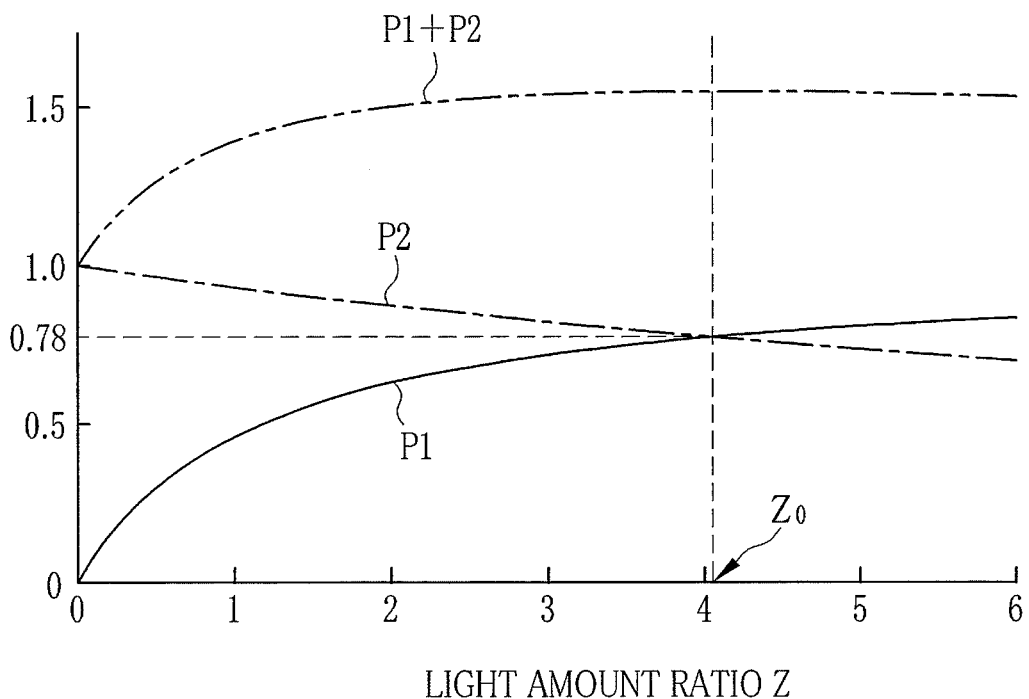
FIG. 16 is a graph showing the rate of a main component of each of first and second mixed pixel signals and the sum of the rates.

Referring to FIG. 12, $a_1 \approx 0.45$, $a_2 \approx 0.98$, $b_1 \approx 0.53$, and $b_2 \approx 0.07$, and therefore $r_1 \approx 0.85$ and $r_2 \approx 14.0$. Substituting these values into the expressions (7) and (8), the proportions P1 and P2 and the sum of the proportions P1 and P2 vary depending on the light amount ratio Z, as shown in FIG. 16. The proportion P1 increases and the proportion P2 decreases with increase in the light amount ratio Z. Both of the proportions P1 and P2 are high as approximately 80% in the vicinity of an intersection point of the proportions P1 and P2, and in other words, both of the violet narrowband light Vn component and the green narrowband light Gn component have improved color separability.

The above optimal light amount ratio $Z_0$ refers to the light amount ratio at which the proportions P1 and P2 are equal. This optimal light amount ratio $Z_0$ is obtained by an operation based on the expressions (7) and (8), and represented by the following expression (9).

$$Z_0 = \sqrt{r_1/r_2} \quad (9)$$

Substituting the above values $r_1$ and $r_2$ into the expression (9) yields $Z_0 \approx 4.06$. In other words, setting the light amount of the violet narrowband light Vn approximately four times as large as the light amount of the green narrowband light Gn makes both of the proportions P1 and P2 at approximately 80% (mixed color components of approximately 20%), and improves the color separability of both of the violet narrowband light Vn component and the green narrowband light Gn component.

Assuming that the calibration is performed, the first and second mixed pixel signals M1v and M2v under independent application of only the violet narrowband light Vn of a light amount $X_i$ and the first and second mixed pixel signals M1g and M2g under independent application of only the green narrowband light Gn of a light amount $Y_i$ are represented by the following expressions (10) to (13):

$$M1v = a_1 X_i \quad (10)$$

$$M2g = a_2 Y_i \quad (11)$$

$$M1g = b_1 Y_i \quad (12)$$

$$M2v = b_2 X_i \quad (13)$$

Substituting the expressions (10) to (13) into the expression (9), the optimal light amount ratio $Z_0$ is represented by the following expression (14):

$$Z_0 = \frac{X_i}{Y_i} \sqrt{\left(\frac{M1g}{M1v}\right) / \left(\frac{M2v}{M2g}\right)} \quad (14)$$

Then, applying the definitions of $R_1=M1g/M1v$, $R_2=M2v/M2g$, $Z_i=X_i/Y_i$ described above to the expression (14) yields the above expression (2).

Next, with the use of the expressions (10) to (13), the correction coefficients $K_1$ and $K_2$ used in the mixed color correction are represented by $K_1=b_2/a_1$ and $K_2=b_1/a_2$, respectively. Applying the correction coefficients $K_1$ and $K_2$ to the expression (3), being a mixed color correction expression, diagonalizes the expression (6), and the first and second mixed pixel signals M1' and M2' after the mixed color correction are represented by the following expressions (15) and (16):

$$M1' = \left(a_1 - \frac{b_1 b_2}{a_2}\right) X = \left(1 - \frac{1}{r_1 r_2}\right) a_1 X \quad (15)$$

$$M2' = \left(a_2 - \frac{b_1 b_2}{a_1}\right) Y = \left(1 - \frac{1}{r_1 r_2}\right) a_2 Y \quad (16)$$

This means that although the mixed color correction eliminates a mixed color component, a signal value of a main component of each of the first and second mixed pixel signals M1' and M2' after the mixed color correction is reduced by a coefficient of $(1-1/(r_1 r_2))$ in comparison with the first and second mixed pixel signals M1v and M2g (see expressions (10) and (11)) by the time-sharing application. In this embodiment, $r_1 r_2 \approx 11.9$ and therefore $(1-1/(r_1 r_2)) \approx 0.92$, so the rate of decrease of the signal value of the main component is of the order of 8%.

Figure 17:
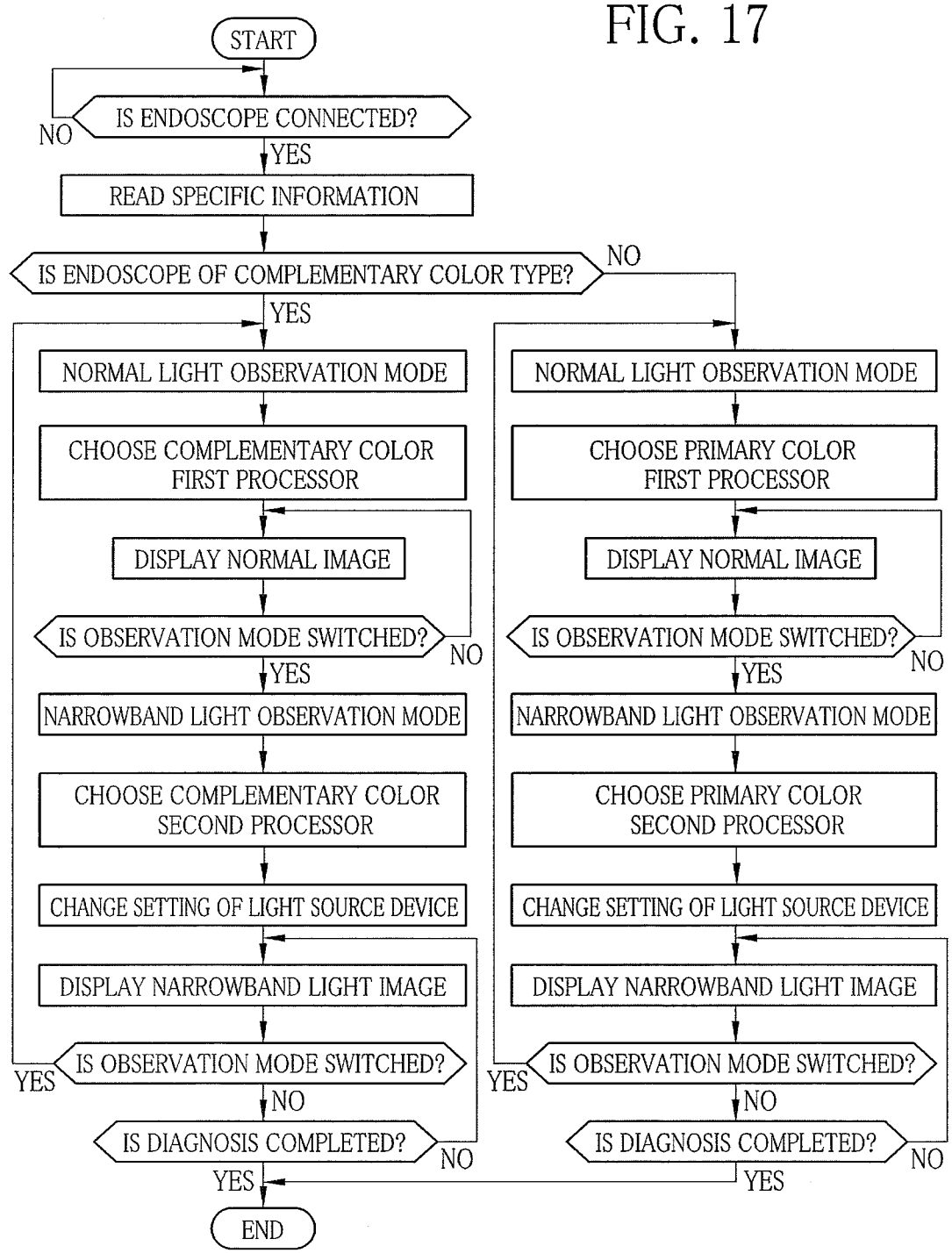
FIG. 17 is a flowchart of the operation of the endoscope system.

Next, the operation of the endoscope system 10 will be described with referring to a flowchart of FIG. 17. Upon connecting the endoscope 13 to the light source device 11 and the processor device 12, the main controller 31 of the processor device 12 reads the specific information from the information storage 30 of the endoscope 13 to judge whether the connected endoscope is the complementary color type endoscope 13a or the primary color type endoscope 13b. For example, in the case of the complementary color type endoscope 13a, the main controller 31 puts the light source device 11 and the processor device 12 into the normal light observation mode, and makes the selector 40 select the complementary color first processor 41 in the signal processing unit 37.

In the normal light observation mode, the dichroic mirror 22 is retracted to a position illustrated by a dotted line in FIG. 5 in the optical combiner 24 of the light source device 11, and the WL-LED 20b is turned on. The normal light (white light) WL from the WL-LED 20b is supplied to the light guide 27 of the complementary color type endoscope 13a. Also, the complementary color type imaging device 28 of the complementary color type endoscope 13a is driven by the imaging controller 32 by the field readout method, and outputs the first to fourth mixed pixel signals M1 to M4. The first to fourth mixed pixel signals M1 to M4 are subjected to the Y/C processing and converted into the RGB signal in the complementary color first processor 41, and displayed on the image display device 14 through the channel allocator 38. Thus, the normal image captured under the normal light is displayed on the image display device 14.

The insert section 16 of the complementary color type endoscope 13a is introduced into a patient's body cavity to perform endoscopy. To inspect the pattern of the superficial blood vessels and the like in tissue to be inspected such as a lesion inside the body cavity, the mode switch 17a is operated. The main controller 31 detects the operation signal of the mode switch 17a, and the light source device 11 and the processor device 12 are put into the narrowband light observation mode.

In the narrowband light observation mode, the selector 40 selects the complementary color second processor 42 and the setting of the light source device 11 is changed. To be more specific, the dichroic mirror 22 is disposed at the intersection point of the optical axes of the V-LED 20a and the WL-LED 20b in the optical combiner 24. At this time, the main controller 31 controls the light source device 21 based on the optimal light amount ratio $Z_0$ contained in the specific information read out of the information storage 30 so as to change the intensity ratio between the V-LED 20a and the WL-LED 20b, such that the violet narrowband light Vn and the green narrowband light Gn exit from the complementary color type endoscope 13a at the light amount ratio Z satisfying the above expression (1).

The V-LED 20a and the WL-LED 20b are simultaneously turned on, and the violet narrowband light Vn and the green narrowband light Gn are mixed in the optical combiner 24. The mixed narrowband light is supplied to the light guide 27 of the complementary color type endoscope 13a. The complementary color type imaging device 28 is driven by the field readout method, and outputs the first to fourth mixed pixel signals M1 to M4. In the complementary color second processor 42, the signal extractor 46 extracts the first and second mixed pixel signals M1 and M2 from the first to fourth mixed pixel signals M1 to M4. Then, the interpolator 47 applies the pixel interpolation processing to the first and second mixed pixel signals M1 and M2, and the mixed color corrector 48 applies the mixed color correction to the first and second mixed pixel signals M1 and M2 and outputs the corrected first and second mixed pixel signals M1' and M2'. The channel allocator 38 assigns the second mixed pixel signal M2' to the R channel and assigns the first mixed pixel signal M1' to the G channel and the B channel, so the first and second mixed pixel signals M1' and the M2' are displayed on the image display device 14. Therefore, the special image captured under the narrowband light is displayed on the image display device 14.

Since the violet narrowband light Vn is transmittable from the surface of the observation object to a first transmission distance in the vicinity of a superficial layer, a first image, which is based on the violet narrowband light Vn, contains much of an image of structure at the first transmission distance, such as the superficial blood vessels. This first image is produced based on the first mixed pixel signal M1. On the other hand, since the green narrowband light Gn is transmittable from the surface of the observation object to a second transmission distance in the vicinity of a middle to deep layer, a second image, which is based on the green narrowband light Gn, contains much of an image of structure at the second transmission distance, such as middle to deep blood vessels. This second image is produced based on the second mixed pixel signal M2. The first image and the second image are combined into the special image.

According to this embodiment, the light amount ratio Z is set based on the optimal light amount ratio $Z_0$ so as to satisfy the expression (1) (preferably, set at $Z=Z_0$). Thus, as shown in FIG. 16, the violet narrowband light Vn component has a high proportion of the first mixed pixel signal M1, and the green narrowband light Gn component has a high proportion of the second mixed pixel signal M2. In other words, since the main component forms a large proportion of each of the first and the second mixed pixel signals M1 and M2, the color separability is improved. Furthermore, the mixed color correction based on the expression (3) further improves the color separability. As described above, the special image according to this embodiment is such an image that the superficial blood vessels have improved contrast and also the middle to deep blood vessels have improved contrast.

The special image is repeatedly displayed until the mode switch 17a is operated or completion operation for completing the endoscopy is performed from the input device 15. Upon operating the mode switch 17a, the endoscope system 10 is put back into the normal observation mode. The completion operation ends the operation.

On the other hand, in a case where the main controller 31 judges that the primary color type endoscope 13b is connected to the light source device 11 and the processor device 12, the light source device 11 and the processor device 12 are put into the normal light observation mode, and the selector 40 selects the primary color first processor 43. In the normal light observation mode, as in the case of the complementary color type, the normal light (white light) WL is produced by the light source device 11 and supplied to the light guide 27 of the primary color type endoscope 13b.

In this case, the primary color type imaging device 29 is driven by the progressive readout method and outputs the RGB signal. This RGB signal is subjected to the pixel interpolation processing and the like in the primary color first processor 43, and displayed on the image display device 14 through the channel allocator 38. Thus, the normal image captured under the normal light is displayed on the image display device 14.

After that, upon operating the mode switch 17a, the light source device 11 and the processor device 12 are put into the narrowband light observation mode. In the narrowband light observation mode, the selector 40 selects the primary color second processor 44, and the setting of the light source device 11 is changed so that the dichroic mirror 22 is disposed at the intersection point of the optical axes of the V-LED 20a and the WL-LED 20b in the optical combiner 24. In this case, in contrast to the complementary color type, the light emission intensity ratio between the V-LED 20a and the WL-LED 20b is set so as to satisfy Z=1. The narrowband light, being the mixture of the violet narrowband light Vn and the green narrowband light Gn, is produced and supplied to the light guide 27 of the primary color type endoscope 13b.

The primary color type imaging device 29 is driven by the progressive readout method and outputs the RGB signal. Out of the RGB signal, the primary color second processor 44 extracts only the B signal and the G signal. The B signal and the G signal are subjected to the pixel interpolation processing and the like, and displayed on the image display device 14 through the channel allocator 38. Thus, the special image captured under the narrowband light is displayed on the image display device 14.

As in the case of the complementary color type, the special image is displayed repeatedly until the mode switch 17a is operated or the completion operation is performed from the input device 15. Upon operating the mode switch 17a, the endoscope system 10 is put back into the normal observation mode. The completion operation ends the operation.

In a case where the complementary color type endoscope 13a is connected to the light source device 11 and the processor device 12, the calibration for recalculating the optimal light amount ratio $Z_0$ can be performed by operation of the input device 15 or the like. In the calibration, a white plate or the like is used as an object to be imaged.

In the calibration, the selector 40 selects the calibration processor 45, and the violet narrowband light Vn and the green narrowband light Gn are applied at the currently used light amount ratio Z in a time sharing manner. The complementary color type imaging device 28 outputs the first mixed pixel signals M1v and M1g and the second mixed pixel signals M2g and M2v, and the calibration processor 45 calculates an average of each signal value. Then, the optimal light amount ratio calculator 39 calculates the optimal light amount ratio $Z_0$ based on the average of each signal value and the currently used light amount ratio Z. The main controller 31 sets the calculated optimal light amount ratio $Z_0$ to the light source device 11, and deletes and replaces the optimal light amount ratio $Z_0$ stored in the information storage 30 of the complementary color endoscope 13a.

The first mixed pixel signals M1v and M1g and the second mixed pixel signals M2g and M2v obtained in the calibration are used for calculating the correction coefficients $K_1$ and $K_2$. The calculated correction coefficients $K_1$ and $K_2$ are written to the information storage 30 of the complementary color type endoscope 13a and used in the next use of the complementary color type endoscope 13a.

Note that, the light amount ratio Z is set by regulating the light emission intensity of the V-LED 20a and the WL-LED 20b in the above embodiments, but may be set by regulating light emission time. Furthermore, both of the light emission intensity and the light emission time may be regulated in order to set the light amount ratio Z.

In the above embodiment, the light amount ratio Z is set based on the optimal light amount ratio $Z_0$ so as to satisfy the expression (1) (preferably, $Z=Z_0$), but the light amount ratio Z may be set smaller than the optimal light amount ratio $Z_0$, namely so as to satisfy the following expression (17). In this case, P2>P1 holds true, and therefore the second image, which is based on the green narrowband light Gn having high reflectivity from the mucosa membrane and the like, is enhanced and the visibility of the mucosa membrane is improved.

$$Z_0(1-\Delta) \leq Z < Z_0 \qquad (17)$$

In the above embodiment, $\Delta$ is set at 0.5. This $\Delta$ is for considering variation in optical characteristics and the like, and arbitrarily changeable to 0.2, 0.3, or the like.

Figure 18:
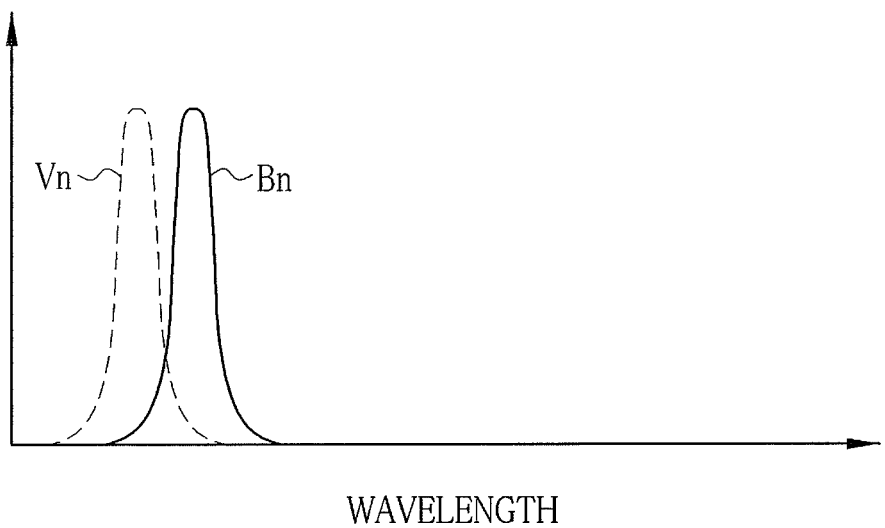
FIG. 18 is a graph showing an emission spectrum of blue narrowband light.

In the above embodiment, the V-LED 20a and the WL-LED 20b are used as the LED light source 20, but a blue LED, which emits blue narrowband light Bn having a wavelength band on a longer side than the violet narrowband light Vn, as shown in FIG. 18, may be used instead of the V-LED 20a. The center wavelength of the blue narrowband light Bn is within the confines of approximately 410 nm to 420 nm, and preferably at approximately 415 nm.

Instead of the V-LED 20a and the WL-LED 20b, a plurality of LEDs (for example, four LEDs) having different emission wavelength bands may be provided. Turning on all the LEDs produces the normal light (white light), while turning on two of the LEDs produces two types of narrowband light. Furthermore, another type of semiconductor light source such as an LD (laser diode) may be used instead of the LED.

Figure 19:
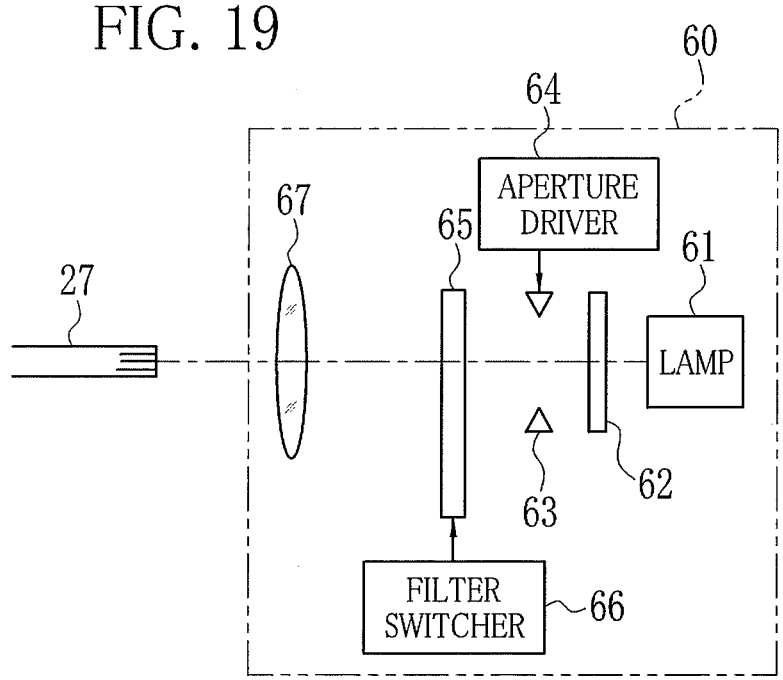
FIG. 19 is a schematic view of a modification example of a light source device.

Another light source device that has a lamp for emitting light having a wide wavelength band such as white light and a narrowband filter may be used instead of the light source device 11 described in the above embodiment. In FIG. 19, a light source device 60 includes a lamp 61, an infrared cut filter 62, an aperture stop 63, an aperture driver 64, a rotary filter unit 65, a filter switcher 66, and a condenser lens 67.

The lamp 61 emits white light WL under the control of the above main controller 31. The infrared cut filter 62 cuts an infrared component out of the white light WL produced by the lamp 61, so the remaining component enters the aperture stop 63. The aperture driver 64 regulates the opening size of the aperture stop 63 to adjust the transmission light amount of the white light WL. This aperture driver 64 is controlled by the dimmer 36 described above.

Figure 20:
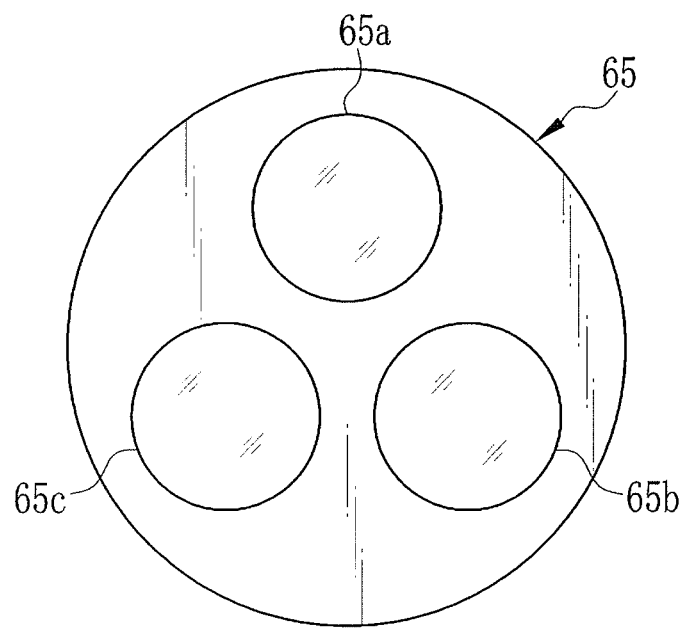
FIG. 20 is a schematic view of a rotary filter unit.

As shown in FIG. 20, the rotary filter unit 65 has a first narrowband filter 65a, a second narrowband filter 65b, and an opening 65c. The filter switcher 66 turns the rotary filter unit 65 under the control of the main controller 31, so that one of the first narrowband filter 65a, the second narrowband filter 65b, and the opening 65c is disposed in an optical axis of the white light WL.

Figure 21:
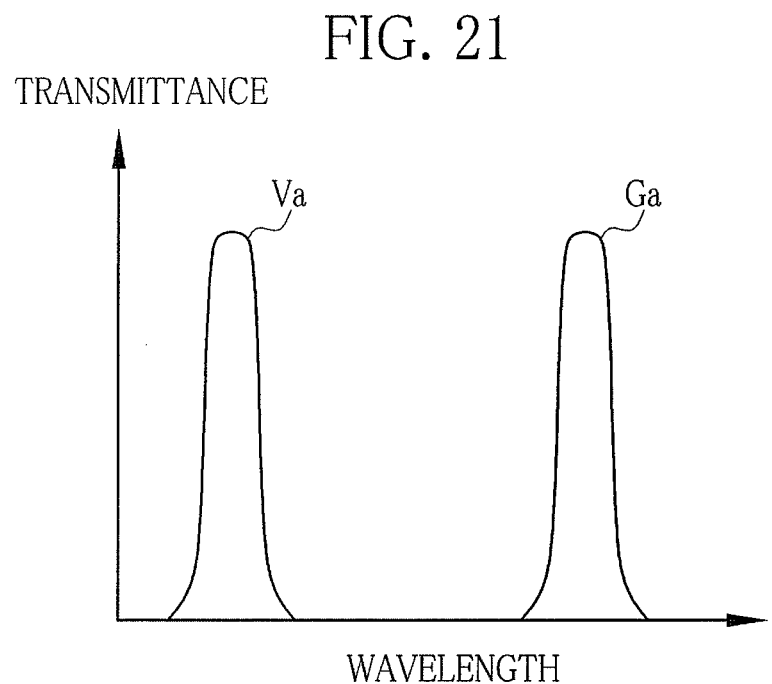
FIG. 21 is a graph showing a transmission characteristic of a first narrowband filter.

As shown in FIG. 21, the first narrowband filter 65a is a two-peak filter, which has a first characteristic section Va having a band-pass characteristic at a first narrowband (a center wavelength of 405 nm) and a second characteristic section Ga having a band-pass characteristic at a second narrowband (a center wavelength of 540 nm). The first characteristic section Va and the second characteristic section Ga have approximately equal transmittance.

This first narrowband filter 65a is disposed in the optical axis of the white light WL, in a case where the narrowband light observation mode is chosen and the endoscope 13 is of the primary color type. Passing the white light WL through the first narrowband filter 65a produces the violet narrowband light Vn and the green narrowband light Gn. The violet narrowband light Vn and the green narrowband light Gn enter the light guide 27 through the condenser lens 67. The light guide 27 has the spectral attenuation characteristic as shown in FIG. 13. The transmittance of the first characteristic section Va may be set a little higher than the transmittance of the second characteristic section Ga in consideration of the spectral attenuation characteristic and the like, so as to substantially equalize the light amounts of the violet narrowband light Vn and the green narrowband light Gn exiting from the light guide 27.

Figure 22:
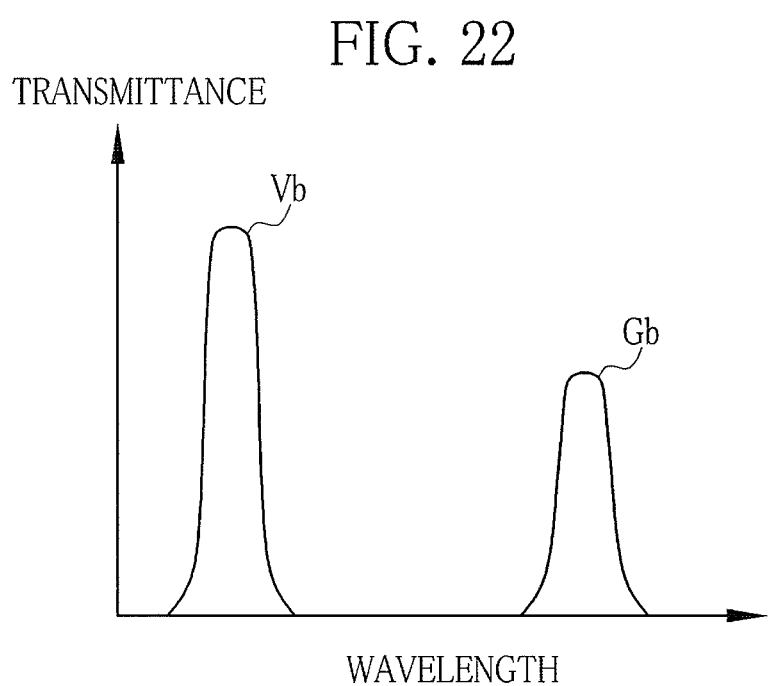
FIG. 22 is a graph showing a transmission characteristic of a second narrowband filter.

As shown in FIG. 22, the second narrowband filter 65b is a two-peak filter, which has a first characteristic section Vb having a band-pass characteristic in a first narrowband and a second characteristic section Gb having a band-pass characteristic in a second narrowband. The first characteristic section Vb and the second characteristic section Gb have much different transmittance.

This second narrowband filter 65b is disposed in the optical axis of the white light WL, in a case where the narrowband light observation mode is chosen and the endoscope 13 is of the complementary color type. Passing the white light WL through the second narrowband filter 65b produces the violet narrowband light Vn and the green narrowband light Gn having a predetermined light amount ratio corresponding to the transmittance ratio between the first and second characteristic sections Vb and Gb. The violet narrowband light Vn and the green narrowband light Gn enter the light guide 27 through the condenser lens 67. The transmittance ratio between the first and second characteristic sections Vb and Gb is set in consideration of the spectral attenuation characteristic of the light guide 27 and the like, such that the light amount ratio Z between the violet narrowband light Vn and the green narrowband light Gn exiting from the light guide 27 satisfies the expression (1) (preferably, $Z=Z_0$).

The opening 65c is disposed in the optical axis of the white light WL in a case where the normal observation mode is chosen. The opening 65c passes the white light WL incident thereon as-is without limiting its wavelength. The white light WL enters the light guide 27 through the condenser lens 67, and exits from the light guide 27 as the normal light.

Figure 23:
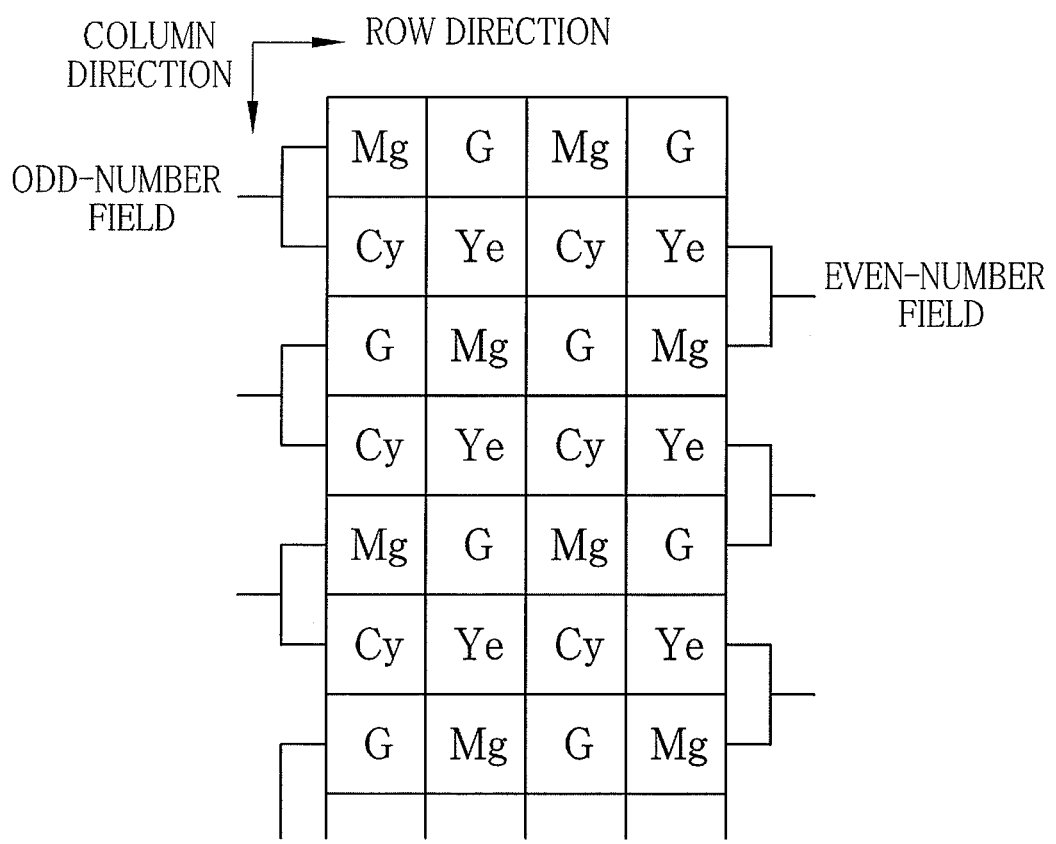
FIG. 23 is a schematic view of a modification example of the complementary color type color separation filter.

The above embodiments use the complementary color type imaging device 28 having the complementary color type color separation filter 28a of the complementary-color checkered-pattern color-difference line sequential method, as shown in FIG. 7, but may use another complementary color type imaging device having another complementary color type color separation filter, as shown in FIG. 23, of the complementary-color checkered-pattern color-difference line sequential method, instead.

In the above embodiments, the combination of the Mg pixel and the Cy pixel composes the first mixed pixel, and the combination of the G pixel and the Ye pixel composes the second mixed pixel. However, the combinations of mixed pixels are not limited to these and arbitrarily changeable.

According to the above embodiments, in the calibration mode, the violet narrowband light Vn and the green narrowband light Gn are applied at the currently used light amount ratio Z in a time-sharing manner, and the optimal light amount ratio $Z_0$ is calculated based on this light amount ratio Z and the signal values of the first and second mixed pixels. Instead of this, the violet narrowband light Vn and the green narrowband light Gn may be applied with stepwise change of the light amount ratio Z in a time-sharing manner, and the above proportions P1 and P2 may be calculated whenever the light amount ratio Z is changed, on the basis of the signal values of the first and second mixed pixels, in order to obtain the optimal light amount ratio $Z_0$ at which the proportions P1 and P2 become equal.

According to the above embodiments, the imaging controller 32, the CDS circuit 33, the A/D converter 34, and the like are contained in the processor device 12, but may be provided in the endoscope 13.

In the above embodiments, the complementary color type imaging device 28 and the primary color type imaging device 29 are constituted of the CCD image sensors, but may be constituted of CMOS image sensors. In the case of the CMOS image sensor, the imaging controller 32, the CDS circuit 33, the A/D converter 34, and the like are formable in a CMOS semiconductor substrate formed with the image sensor.

According to the above embodiments, both of the complementary color type endoscope and the primary color type endoscope are connectable to the light source device and the processor device, but only the complementary color type endoscope may be connectable thereto.

In the above embodiments, the light source device and the processor device are configured as independent devices, but may be formed into a single device. Furthermore, the light source device may be incorporated in the endoscope.

Note that, "lighting section" described in claims corresponds to a combination of "light source device" and "optical members (light guide, lighting lens, and the like) for leading light from the light source device and applying the light to an observation object" described in the embodiments.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
   a complementary color type imaging device having a first mixed pixel and a second mixed pixel, each of said first mixed pixel and said second mixed pixel sensing both of first narrowband light having a center wavelength in a blue or violet wavelength range and second narrowband light having a center wavelength in a green wavelength range, a first mixed pixel signal being read from said first mixed pixel, a second mixed pixel signal being read from said second mixed pixel; and
   a lighting section having a light source device for simultaneously applying said first and second narrowband light to an observation object, a light amount ratio of said first narrowband light to said second narrowband light being set within a predetermined range based on an optimal light amount ratio, at said optimal light amount ratio a proportion of a first narrowband light component within said first mixed pixel signal being equal to a proportion of a second narrowband light component within said second mixed pixel signal,
   wherein said light amount ratio is set at a value "Z" satisfying expression (a) as follows:

$$Z_0(1-\Delta) \leq Z \leq Z_0(1+\Delta) \quad (a)$$

wherein, $Z_0$ represents said optimal light amount ratio defined by $Z_0 = Z_i(R_1/R_2)^{1/2}$, and $\Delta = 0.5$, and $R_1$ represents a ratio of a signal value of said first mixed pixel under independent application of only said second narrowband light to a signal value of said first mixed pixel under independent application of only said first narrowband light, and $R_2$ represents a ratio of a signal value of said second mixed pixel under independent application of only said first narrowband light to a signal value of said second mixed pixel under independent application of only said second narrowband light, and $Z_i$ represents the ratio of the light amount of said first narrowband light to the light amount of said second narrowband light in said independent application.

2. The endoscope system according to claim 1, wherein said complementary color type imaging device has a matrix of at least four types of pixels for performing photoelectric conversion of light of different colors, and two types of said four types of pixels next to in a vertical scan direction compose said first mixed pixel, and other two types of said four types of pixels next to in said vertical scan direction compose said second mixed pixel.

3. The endoscope system according to claim 2, wherein said complementary color type imaging device has a complementary color type color separation filter of a complementary-color checkered-pattern color-difference line sequential method having color filter segments of cyan, magenta, yellow, and green;
   said first mixed pixel is a combination of a magenta pixel and a cyan pixel, and said second mixed pixel is a combination of a green pixel and a yellow pixel; and
   said first narrowband light has a center wavelength in a blue or violet wavelength range, and said second narrowband light has a center wavelength in a green wavelength range.

4. The endoscope system according to claim 3, further comprising:
   a channel allocator for assigning said signal value of said first mixed pixel to a B channel and a G channel of an image display device, and assigning said signal value of said second mixed pixel to an R channel of said image display device, to display a special image.

5. The endoscope system according to claim 1, wherein said ratio $R_1$ is a value in which the average of said signal values of said first mixed pixels under independent application of only said second narrowband light is divided by the average of said signal values of said first mixed pixels under independent application of only said first narrowband light; and
   said ratio $R_2$ is a value in which the average of said signal values of said second mixed pixels under independent application of only said first narrowband light is divided by the average of said signal values of said second mixed pixels under independent application of only said second narrowband light.

6. The endoscope system according to claim 1, wherein said light amount ratio is set at a value "Z" satisfying the expression (b) as follows:

$$Z_0(1-\Delta) \leq Z < Z_0 \quad (b).$$

7. The endoscope system according to claim 1, wherein said light amount ratio is set so as to be equal to said optimal light amount ratio.

8. The endoscope system according to claim 1, wherein a complementary color type endoscope having said complementary color type imaging device and a primary color type endoscope having a primary color type imaging device are detachably connected to said light source device.

9. The endoscope system according to claim 8, further comprising:
   a controller for controlling said light source device such that said light amount ratio is set at a larger value in a case where said complementary color type endoscope is connected to said light source device than in a case where said primary color type endoscope is connected to said light source device.

10. The endoscope system according to claim 9, wherein said controller sets said light amount ratio at "1" in a case where said primary color type endoscope is connected to said light source device, while said controller sets said light amount ratio at "Z" satisfying said expression (a) in a case where said complementary color type endoscope is connected to said light source device.

11. The endoscope system according to claim 9, wherein each of said complementary color type endoscope and said primary color type endoscope has information storage for storing specific information; and
    said controller reads out said specific information from said information storage of said complementary color type endoscope or said primary color type endoscope that is connected to said light source device, in order to judge the type of said connected endoscope.

12. The endoscope system according to claim 11, wherein said information storage of said complementary color type endoscope stores said optimal light amount ratio; and
    in a case where said complementary color type endoscope is connected to said light source device, said controller determines said light amount ratio based on said optimal light amount ratio read out of said information storage.

13. The endoscope system according to claim 12, wherein said endoscope system has a calibration mode for calculating said optimal light amount ratio under applying said first and second narrowband light independently from said light source device; and said controller stores said optimal light amount ratio calculated in said calibration mode to said information storage of said complementary color type endoscope connected to said light source device.

14. The endoscope system according to claim 9, wherein said light source device includes a plurality of LEDs; and
said controller sets said light amount ratio by regulating at least one of light emission intensity and light emission time of said plurality of LEDs.

15. The endoscope system according to claim 1, further comprising:
a corrector for correcting a signal value M1 of said first mixed pixel and a signal value M2 of said second mixed pixel on the basis of expressions (c) and (d) as follows:

$$M1'=M1-K_2 \times M2 \quad (b)$$

$$M2'=M2-K_1 \times M1 \quad (c)$$

wherein, $K_1$ represents the ratio of said signal value of said second mixed pixel to said signal value of said first mixed pixel under independent application of only said first narrowband light, $K_2$ represents the ratio of said signal value of said first mixed pixel to said signal value of said second mixed pixel under independent application of only said second narrowband light.

16. An endoscope system comprising:
a complementary color type imaging device having a first mixed pixel and a second mixed pixel, each of said first mixed pixel and said second mixed pixel sensing both of first narrowband light having a center wavelength in a blue or violet wavelength range and second narrowband light having a center wavelength in a green wavelength range, a first mixed pixel signal being read from said first mixed pixel, a second mixed pixel signal being read from said second mixed pixel; and a lighting section having a light source device for simultaneously applying said first and second narrowband light to an observation object, a light amount ratio of said first narrowband light to said second narrowband light being set within a predetermined range based on an optimal light amount ratio, at said optimal light amount ratio a proportion of a first narrowband light component within said first mixed pixel signal being equal to a proportion of a second narrowband light component within said second mixed pixel signal, wherein said light amount ratio is set at a value "Z" satisfying expression (e) as follows:

$$Z_0(1-\Delta) \leq Z < Z_0(1+\Delta) \quad (e)$$

wherein, $Z_0$ represents said optimal light amount ratio defined by $Z_0=(r_1/r_2)^{1/2}$, and $\Delta=0.5$, and $r_1$ is a value in which the sensitivity of said first mixed pixel to said first narrowband light is divided by the sensitivity of said first mixed pixel to said second narrowband light, and $r_2$ is a value in which the sensitivity of said second mixed pixel to said second narrowband light is divided by the sensitivity of said second mixed pixel to said first narrowband light.

17. A light source device comprising:
a light source for simultaneously producing first narrowband light and second narrowband light having a longer wavelength than said first narrowband light and supplying said first and second narrowband light to an endoscope; and a light source controller for controlling said light source, wherein a complementary color type imaging device from which a first mixed pixel and a second mixed pixel are read out is connectable to said light source device, and said first mixed pixel and said second mixed pixel sense both of said first narrowband light having a center wavelength in a blue or violet wavelength range and said second narrowband light having a center wavelength in a green wavelength range; and a light amount ratio of said first narrowband light to said second narrowband light is set within a predetermined range based on an optimal light amount ratio, and at said optimal light amount ratio, a proportion of a first narrowband light component within a first mixed pixel signal is equal to a proportion of a second narrowband light component within a second mixed pixel signal, wherein said light amount ratio is set at a value "Z" satisfying expression (a) as follows:

$$Z_0(1-\Delta) \leq Z \leq Z_0(1+\Delta) \quad (a)$$

wherein, $Z_0$ represents said optimal light amount ratio defined by $Z_0=Z_i(R_1/R_2)^{1/2}$, and $\Delta=0.5$, and $R_1$ represents a ratio of a signal value of said first mixed pixel under independent application of only said second narrowband light to a signal value of said first mixed pixel under independent application of only said first narrowband light, and $R_2$ represents a ratio of a signal value of said second mixed pixel under independent application of only said first narrowband light to a signal value of said second mixed pixel under independent application of only said second narrowband light, and $Z_i$ represents the ratio of the light amount of said first narrowband light to the light amount of said second narrowband light in said independent application.

* * * * *